(12) United States Patent
Lustig et al.

(10) Patent No.: US 7,373,259 B2
(45) Date of Patent: May 13, 2008

(54) METHOD AND APPARATUS FOR PERFORMING CHEMICAL REACTIONS IN A PLURALITY OF SAMPLES

(75) Inventors: Steve R. Lustig, Landenberg, PA (US); Gary W. Foggin, Wilmington, DE (US); Robert Agreen, New Castle, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 461 days.

(21) Appl. No.: 10/653,757

(22) Filed: Sep. 3, 2003

(65) Prior Publication Data

US 2004/0156757 A1 Aug. 12, 2004

Related U.S. Application Data

(60) Provisional application No. 60/407,899, filed on Oct. 29, 2002.

(51) Int. Cl.
*G06F 19/00* (2006.01)
(52) U.S. Cl. .......................................... 702/31; 702/30
(58) Field of Classification Search ................ 702/31, 702/30; 436/46, 179; 703/31
See application file for complete search history.

(56) References Cited

U.S. PATENT DOCUMENTS

| | | | | |
|---|---|---|---|---|
| 4,027,979 A * | 6/1977 | Komarniski | ................ | 356/409 |
| 5,510,151 A * | 4/1996 | Matsuyama et al. | ........ | 427/509 |
| 6,679,103 B1 * | 1/2004 | Sadler | ........................... | 73/73 |
| 6,962,644 B2 * | 11/2005 | Paterson et al. | ....... | 156/345.28 |
| 7,250,303 B2 * | 7/2007 | Jakubowicz et al. | .......... | 436/54 |
| 2002/0016006 A1 | 2/2002 | Wendelbo et al. | | |
| 2002/0042140 A1 | 4/2002 | Hagemeyer et al. | | |
| 2003/0202911 A1 * | 10/2003 | Erden et al. | ................ | 422/130 |

FOREIGN PATENT DOCUMENTS

| | | |
|---|---|---|
| EP | 1 226 867 | 7/2002 |
| GB | 1 548 488 | 7/1979 |
| WO | WO 0029844 | 5/2000 |
| WO | WO 0051720 | 9/2000 |
| WO | WO 01/07896 | 2/2001 |

* cited by examiner

*Primary Examiner*—John Barlow
*Assistant Examiner*—Douglas Washburn

(57) ABSTRACT

A method and apparatus for simultaneously performing chemical reactions and determining molecular transport dynamics on a plurality of samples such as thin film samples. The apparatus of the present invention is capable of containing multiple samples in individual sample holding positions in a sample holder within a housing and maintaining those holding positions in chemical isolation from each other. Under control of a computerized controller, the apparatus positions the sample holder so that each sample holding position may be positioned adjacent to one or more ports connected to a distribution manifold. The apparatus exposes each sample to one or more fluids in liquid or gas phase, thereby carrying out a chemical reaction and/or determining molecular transport dynamics under controlled temperature and pressure conditions. The sample holding positions may be positioned in an analytical measurement station within the housing so that the resulting chemical compound or mixture may be characterized.

10 Claims, 38 Drawing Sheets

FIG. 19A

BUTTON SETUP
    Button Set Points
        Form Set Points
            Function Activate Omegas > Initiates software communication link between this application and the temperature controllers for the reactor and process Function Save Set Points > The user enters the temperature set point, maximum safety limit temperature and check box to activate each temperature zone in the reactor or process. This function then stores these settings as the new defaults as well as in records describing the experiment.

Function Send Set Points

> Sends the temperature set points, safety limits and enable flag data to the temperature controller.

Function Dismiss

> Removes this form window from the computer screen.

Button DataPath
        Form DataPath
            Function Make Directory

> Creates a new directory to store data files and records associated with an experiment.

Continued from Fig. 19A

Function Apply

> Sets the storage directory for data files as the path selected in the displayed directory box.

Function Dismiss

> Removes this form window from the computer screen.

Button Motor
    Form Motor
        Function Go

> Directs the motor to send the sample position to the optical measurement position.

Function Go To Load Position

> Directs the motor to send the sample canoe to the load position.

Function Record Settings

> Stores in memory which sample positions will be observed/skipped during an experimental run loop.

Function Update Status

> Updates the displayed status attributes of the motor, such as permission to move, current position, limit indicators, position error, motor overheating and motor power.

Continued from Fig. 19B

Function Stop Motor Now

> Sends an immediate message to the positioning motor to stop moving.

Function Dismiss

> Removes this form window from the computer screen.

Button Calibrate Motor

Form Calibrate motor

Function Update Status

> Updates the displayed status attributes of the motor, such as current location, home limit indicator, permission to move and position error.

Function Go

> Directs the motor to send the selected sample position to the optical measurement position.

Function Set Sample Location @ Current

> Stores in memory the current absolute motor position as the location at which the selected sample position is in the optical measurement position.

Function Nudge the Motor

> Directs the motor to move the sample canoe in the relative direction and distance indicated by the slider.

Function Stop Motor Now

> Sends an immediate message to the positioning motor to stop moving

Continued from Fig. 19C

Function Go There

> Directs the motor to move the sample canoe to the absolute position entered in the text box.

Function Find Diode

> Directs the motor to move the sample canoe toward the reactor opening and stop when it reaches the home diode indicator.

Function Find Load position

> Same as Find Diode, but also travels to the load position, where the samples are positioned in the load/unloading gas manifold.

Function Record All Parameters and Reset Motor

> Stores all motor control parameters and positions in a permanent configuration file and sends these parameters to the motor memory.

Function Read Control Parameters

> Reads the current motor parameters in the motor memory. Displays these values in a new pop-up window.

Function Dismiss

> Removes this form window from the computer screen.

FIG. 20A

Button Ocean Optics
    Form Ocean Optics
        Function Correct Dark

> Activates internal circuitry in the UV/Vis spectrometer to correct for purely-electronic, dark signal error.

Function View Test

> Collects all immediate UV/Vis spectrum and displays the spectrum in a pop-up window.

Function Apply Settings

> Stores UV/Vis spectrometer settings entered in the form to the spectrometer hardware, computer memory and configuration files.

Function Dismiss

> Removes this form window from the computer screen.

Button Nicolet
    Form Nicolet
        Function Bench Set Up

> Activates FTIR spectrometer software to configure the FTIR processor, optical assembly and associated hardware.

Function Invoke OMNIC

> Activates vendor FTIR software for data visualization and processing.

Continued from Fig. 20A

Function Apply Settings

> Stores all FTIR spectrometer settings entered in the form to the spectrometer hardware, computer memory and configuration files.

Function Dismiss

> Removes this form window from the computer screen.

FIG. 21A

Button Parameters
   Form Parameters
      Button Set Path
         Form DataPath
           Function Write Experiment File > Records all parameters and settings in a configuration file which would be required to describe and reproduce exactly the current experiment.

Button Head Settings Experiment File

> Opens the Read Setting Experiment File form.

Form Read Settings Experiment File
      Function Read

> Restores a complete set of parameters and settings from the previously written experiment file displayed in the file directory box.

Function Read + Set Path

> Same as Function Read, but also sets the directory to store new data as the same directory as the experiment file to be selected and read Function Dismiss > Removes this form window from the computer screen.

Continued from Fig. 21A

Button Set Motor Positions

Form Motor

Function Refresh

> Updates the listing of all experimental setting and parameter values listed in the text area in the upper right section of this form.

Function Dismiss

> Removes this form window from the computer screen.

FIG. 22

Button Configuration

Form Configuration

Function Record These Ports

> Permits the user to assign computer serial port numbers to the interfaced instrumentation, such as the motor, UV/Vis spectrometer, temperature controllers and analog/digital signal converter Function Record These Names > Permits the user to assign zone names to pressure and temperature sensing signals.

Function Check Installation

> Runs a test to ensure the software and its requisite resources are installed, configured and working properly.

Function Dismiss

> Removes this form window from the computer screen.

FIG. 23A

Button Process
    Button Open/Close Valves
        Form Open/Close Valves
            Function Send > Transmits signals to the solenoids to either open or close the Load In and Load Out valves, depending on the radio button selections on the form.

Function Dismiss

> Removes this form window from the computer screen.

Button SetPoints
        Form SetPoints
    Button Show Process
        Form Show Process
            Function Update > Displays the current temperature and pressure zone names and attributes, such as control set point, current value, maximum limit, enable status and heating power output.

Function Dismiss

> Removes this form window from the computer screen.

Continued from Fig. 23A

Function Auto-Tune Omegas(!)

> Initiates the temperature controller firmware which begins heating the process zones while computing optimal PID controller parameters Function Show Process Logs > Displays a pop-up window which displays the recent history of process temperatures process pressures, system messages and experimental events.

FIG. 24A

Button Experiment
   Button Parameters
      Form Parameters
   Button Apply
      Function Apply > Updates and records all parameters and settings in memory which would be required to describe and reproduce exactly the current experiment.

Button Run !!
      Function Run

> Activates the automated run sequence for an experiment. The run sequence is displayed in the Parameters form.

Button Pause
      Function Pause

> Pauses the automated run sequence or Resumes the current run sequence.

Button Data
      Button View IR Spectrum
         Function View IR Spectrum

> Activates vendor software to display and analyze a recorded FTIR spectrum.

Continued from Fig. 24A

Button Analyze IR Series

Form Analyze IR Series

Function Select

> Use the data in the file currently selected in the file list box as a background reference to compute new peak heights and areas.

Function View

> Display the data in the file currently selected in the file list box as a spectrum with the previously selected background reference. The user may select regions to define the appropriate baseline and peak integration limits.

Function Apply

> Record and use the previously selected baseline and peak integration limit.

Function Process

> For the data in each file over the range of files selected in the form, integrate the absorbance peak using the background, baseline and limit specifications displayed in the form. Write the collection time and peak area data in a result file.

Continued from Fig. 24B

Function View Data

> Invoke a Notepad editor to view the aforementioned result file.

Function Dismiss

> Removes this form window from the computer screen.

Button Export IR Series

Form Export IR Series

Function Make Dir

> Create a new directory in which will be generated.

Function Run

> Convert the data in the selected file sequence from their current data format into the format selected in the list box. Store each data file set in a new file with the same file name and new format suffix.

Function Dismiss

> Removes this form window from the computer screen.

FIG. 25A

Button View UV/Vis Spectrum
    Function Invoke UV/Vis

> Begin the execution of a program to view UV/Vis spectra recorded during a previous experiment.

Button Analyze UV/Vis Series
    Function Invoke UV/Vis

> Begin the execution of a program to analyze UV/Vis spectra and absorptions recorded during a previous experiment.

Button Export UV/Vis Series
    Function Invoke UV/Vis

> Begin the execution of a program to convert data in one format to another.

Button Set Motor's Home Position
    Form Set Motor's Home Position
        Button Sample Boat is Intalled
            Function Sample Boat is Installed > Motor is safe to operate. The function begins a sequence to find the sample canoe standard load position. If the sequence is successful, permission is granted to move the motor.

Button Cancel
           Function Cancel

> The user selects this button when he cannot confirm that the sample boat is properly loaded. The software does not set the home position and does not grant permission to move the motor.

Continued from Fig. 25A

Button Emergency Motor Stop
    Function Emergency Motor Stop

> The motor is sent an immediate message to stop motion. the experiment is terminated and the program is terminated.

Button Exit and Kill
    Form Exit and Kill
        Function Exit

> The user confirms that he wishes to terminate the program.

Function Cancel

> Removes this form window from the computer screen.

FIG. 26

KEY:

The Software follows the familiar windows, event-driven mode of operation. The software does nothing until the user presses a button. The button pressing event may alter the viewable buttons or activate Forms and Functions. Forms and Functions ae encoded as software subroutines. The various buttons and functions ae identified by the label observed by the user on the forms.

Form

> A form presents a window on the user's computer screen. This form may present information, controls, input objects (such as text boxes, radio buttons, menus, lists, sliders), pictures, and command buttons.

Button

> A button (or command button) is pressed to execute a software command. The button typically begins the execution of a function, but may also expose new forms or replace the current set of viewable buttons.

Function

> A function initiates the execution of a software module which is typically a Visual Basic subroutine or function.

METHOD AND APPARATUS FOR PERFORMING CHEMICAL REACTIONS IN A PLURALITY OF SAMPLES

This application claims the benefit of U.S. Provisional Application No. 60/407,899 filed Oct. 29, 2002, which is incorporated in its entirety as a part hereof for all purposes.

FIELD OF THE INVENTION

This invention relates to an apparatus for screening a plurality of sample materials for chemical activity, chemical equilibrium, and/or molecular transport.

BACKGROUND OF THE INVENTION

Screening candidate materials for chemical activity, for molecular transport, or for potentially catalytic properties is a time-consuming, labor-intensive process. Obtaining information concerning reaction rates at various compositions and process conditions, such as different temperatures and pressures, requires systematic investigation and the performance of many experiments.

An apparatus that could at least partially automate the process of simultaneously carrying out multiple reactions and simultaneously or sequentially making spectroscopic measurements to obtain information about reaction and molecular transport dynamics is considered to be advantageous. The present invention provides such an apparatus.

SUMMARY OF THE INVENTION

This invention relates to a method and apparatus for simultaneously performing chemical reactions and simultaneously or sequentially making spectroscopic or other measurements on a plurality of samples, such as thin film samples. The apparatus of the present invention is capable of containing multiple samples in individual sample holding positions in a sample holder within a housing and maintaining those holding positions in chemical isolation from each other. Under control of a computerized controller, the apparatus positions the sample holder so that each sample holding position may be positioned adjacent to one or more ports connected to a distribution manifold. The apparatus exposes each sample to one or more fluids in liquid and/or gas phase, thereby carrying out a chemical reaction under controlled temperature, composition and pressure conditions. The sample holding positions may be positioned in a measurement station, such as an optical measurement station, within the housing so that the resulting chemical state may be characterized. Chemical reactions may be carried out within the measurement station and the chemical reaction and molecular transport dynamics may be monitored in real time.

Another embodiment of this invention is a method for testing a plurality of samples, by (a) simultaneously reacting all samples with a fluid, and (b) during the reaction of the samples with the fluid, subjecting each sample in sequence to analysis.

Yet another embodiment of this invention is a method for testing a plurality of samples, by (a) simultaneously reacting all samples with a fluid in a sealed vessel, and (b) after completion of the reaction of the samples with the fluid, subjecting each sample in sequence to analysis in the sealed vessel.

A further embodiment of this invention is a method for testing a group of samples, by (a) simultaneously reacting all samples with a fluid in a sealed vessel, (b) before or after step (a), simultaneously reacting one or more members of a subgroup of the group of samples with a fluid in the sealed vessel, and (c) subjecting each sample to analysis.

A further embodiment of this invention is a method for testing a plurality of samples, by (a) bringing all samples to a predetermined temperature in a first chamber of a vessel, (b) simultaneously exposing each sample in a second chamber of the vessel, which is isolated from the first chamber, to a reactive fluid, and (c) subjecting each sample to analysis.

A further embodiment of this invention is a method for testing a plurality of samples, by (a) simultaneously exposing all samples to a non-reactive fluid in a first chamber of a vessel, (b) simultaneously exposing all samples in a second chamber of the vessel, which is isolated from the first chamber, to a reactive fluid, and (c) subjecting each sample to analysis.

A further embodiment of this invention is a method for testing a group of samples in a sealed vessel, by (a) placing one or more members of the group of samples in a position in the vessel to receive separate exposure to a reactive fluid, (b) simultaneously exposing those samples to the fluid, and (c) subjecting in the sealed vessel each member of the group of samples to analysis.

A further embodiment of this invention is an apparatus for testing a group of samples that includes (a) a fluid distribution system to simultaneously expose each sample to a reactive fluid, and (b) a holder for the group of samples slidable with respect to the fluid distribution system, and (c) an analyzer.

A further embodiment of this invention is an apparatus for testing a group of samples that includes (a) a fluid distribution system to simultaneously expose each sample to a reactive fluid, (b) an analyzer, and (c) a holder for the group of samples slidable with respect to the analyzer.

A further embodiment of this invention is an apparatus for testing a group of samples that includes (a) a fluid distribution system to simultaneously expose only the members of a subgroup of the group of samples to a reactive fluid, and (b) a holder for the group of samples slidable with respect to the fluid distribution system, and (c) an analyzer.

A further embodiment of this invention is an apparatus for testing a group of samples that includes (a) a fluid distribution system to simultaneously expose only the members of a subgroup of the group of samples to a reactive fluid, (b) an analyzer, and (c) a holder for the group of samples slidable with respect to the analyzer.

A further embodiment of this invention is a sealed vessel for testing a plurality of samples that includes (a) a fluid distribution system to simultaneously expose the samples to a reactive fluid, and (b) an analyzer in the sealed vessel that is isolated from the fluid distribution system.

A further embodiment of this invention is an apparatus for testing a plurality of samples that includes (a) a first chamber in which each samples is simultaneously exposed to a non-reactive fluid, (b) a second chamber, isolated from the first chamber, in which each samples is simultaneously exposed to a reactive fluid, and (c) an analyzer.

A further embodiment of this invention is an apparatus for testing a plurality of samples that includes (a) a first chamber in which each samples is simultaneously brought to a pre-determined temperature, (b) a second chamber, isolated from the first chamber, in which each samples is simultaneously exposed to a reactive fluid, and (c) an analyzer.

A further embodiment of this invention is an apparatus for testing a plurality of samples that includes (a) a holder for the samples, (b) a cover for the holder, and (c) an analyzer, wherein the cover is slidable with respect to the holder, and the holder is slidable with respect to the analyzer.

A further embodiment of this invention is an apparatus for testing a group of samples that includes (a) a fluid distribution system to simultaneously expose each sample to a reactive fluid; (b) a reaction chamber in which each sample is reacted with the fluid, the reaction chamber for each sample being separate and isolated from the reaction chamber for each other sample; and (c) an analyzer.

BRIEF DESCRIPTION OF THE DRAWINGS

FIG. 19 is a block diagram showing a main control routine for controlling the computer controller.

FIG. 20 is a block diagram showing a control routine for controlling the spectrometer of an optical measurement system.

FIG. 21 is a block diagram showing a routine for recording parameters and settings.

FIG. 22 is a block diagram showing a routine for configuring elements of the system.

FIG. 23 is a block diagram showing a routine for controlling valves and displaying set-points.

FIG. 24 is a block diagram showing a routine for recording parameters and experimental data.

FIG. 25 is a block diagram showing a routine for displaying spectral data.

FIG. 26 is a block diagram showing a routine for controlling the positioning system.

DETAILED DESCRIPTION OF THE INVENTION

Figure 1:
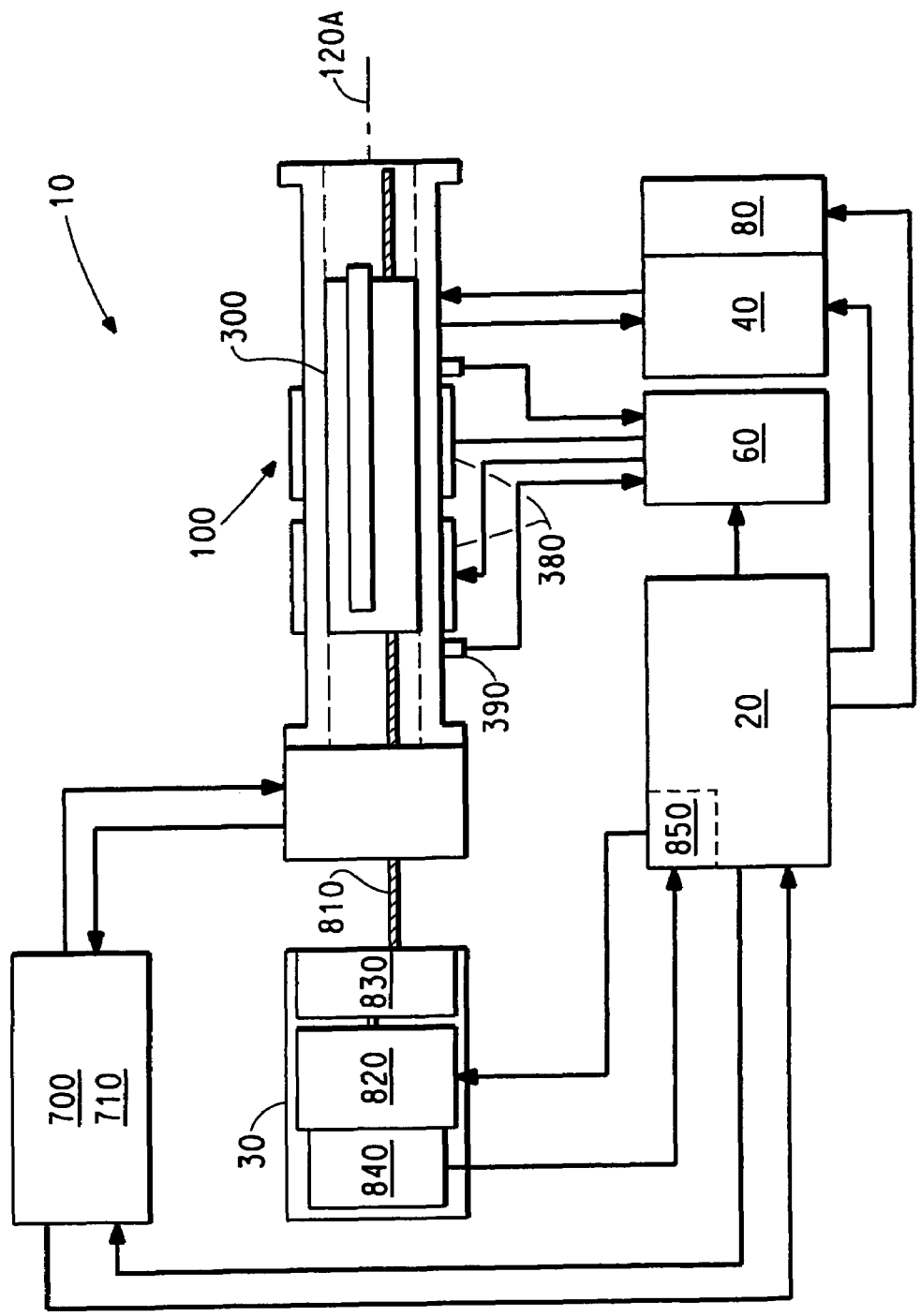
FIG. 1 is a block diagram showing the elements of the apparatus of the present invention.

In accordance with the present invention, a reaction apparatus containing a sample holder is arranged so that a plurality of samples to be reacted may be loaded into the sample holder, each sample being loaded respectively into a separate sample holding position in the sample holder. The sample holder is removable from the reaction apparatus to permit loading the samples in a controlled environment. When loaded, the sample holder may be inserted into an inner body of the reaction apparatus when the inner body is in a loading position. A mechanical detent assembly holds the sample holder in place in the inner body.

The sample holder, as carried within the inner body, may be loaded into the reaction apparatus through a loading/unloading section of the reactor apparatus. The loading/unloading section may be sealed with a manually installed cover. After the loading/unloading section is sealed with the cover, a gas control system is available to purge the loading/unloading section to eliminate any undesired gas within the reactor assembly.

Automated systems, as controlled by a computer, then set the parameters for a reaction, and cause the reaction to occur. A pressure control system may be commanded to bring the pressure and gas concentration in the reactor to a desired level. A temperature control system may be commanded to bring the temperature of the samples in the sample holder to a desired temperature, and a controller may command a fluid control system to introduce reaction fluid(s), which may be one or more gas(es) and/or liquid(s). A controller then commands a drive system to pull the inner body and the sample holder into the reactor housing into a fully inserted reaction position, and commands a positioning system to move the inner body into a selected position within the reaction section of the housing.

A variety of sample holders may be employed. When the samples are analyzed by an optical method, an example of one type of suitable sample holder receives thin film samples mounted on either light absorbing, light transmitting or light reflecting substrates. The substrate may be planar or may contain a well to hold the sample. An example of a second type of optical sample holder receives samples mounted on a substrate, with an attenuated total internal reflection (ATR) crystal in contact with each sample, and has a clamping assembly that clamps the ATR crystal to the sample so that optical contact is maintained. Other kinds of sample holders may be used when other kinds of analytical measurements are made.

The protocol for the chemical reaction environment and the measurements are carried out under control of a control computer. Before the reaction begins, the sample positions may be flushed with an inert, non-reactive gas such as nitrogen. During the reaction phase, a positioning system moves the sample holder, held within the inner body, to a reaction position. The positioning system then moves the sample holder to an analytical monitoring section, and successively positions each sample at the correct position for analytical measurement during or, after completion of, the reaction. The arrangement for the desired type of analysis (i.e. the necessary equipment, commands and activating resources) is then engaged, and analytical measurement of each sample is performed to characterize the reacted sample. After measurement is completed, the sample holder is again brought to the loading/unloading section where, if necessary, the samples may be flushed with an inert gas, the temperature may be raised or lowered to terminate the reaction, and the pressure returned to ambient pressure, such as to atmospheric pressure.

FIG. 1 is a block diagram that illustrates the elements of the apparatus of the present invention. The system 10 contains a computer controller 20, such as an Optiplex GX1 from Dell Computer; an associated positioning system 30; a fluid distribution system 40; a temperature control system 60; a pressure control system 80; and a reaction apparatus 100. The fluid distribution system 40 may contain one or more electrically activated valves capable of controlling the passage of a fluid such as a gas or liquid, such as Swagelok model SS-4BG-3C gas valve, and associated tubing. The temperature control system may contain a commercially available temperature controller, such as a model CN3390 from Omega Corp. Stratford, Conn., heating bands such as Type A heating bands manufactured by Watlow, Inc., and associated RTD temperature sensors, such as model DRW713237, and type J thermocouples, available from Technical Industrial Products. The pressure control system 80 may contain commercially available components such as a compressed gas supply, one or more electrically controlled pressure regulators, and electrically activated gas valves, such as Swagelok model SS-4BG-3C.

Figure 2:
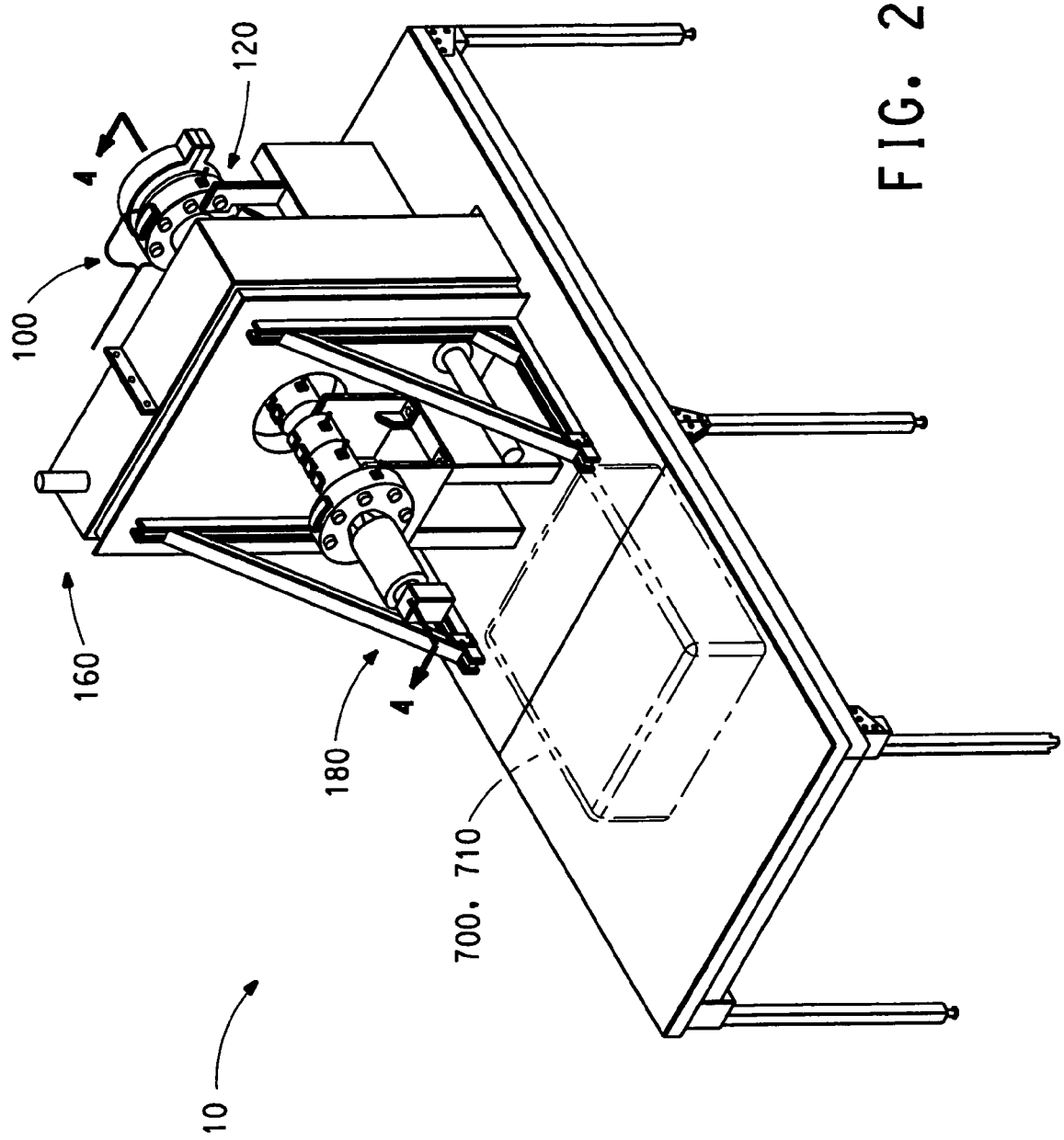
FIG. 2 is a perspective view of the overall reaction apparatus of the present invention.
Figure 3:
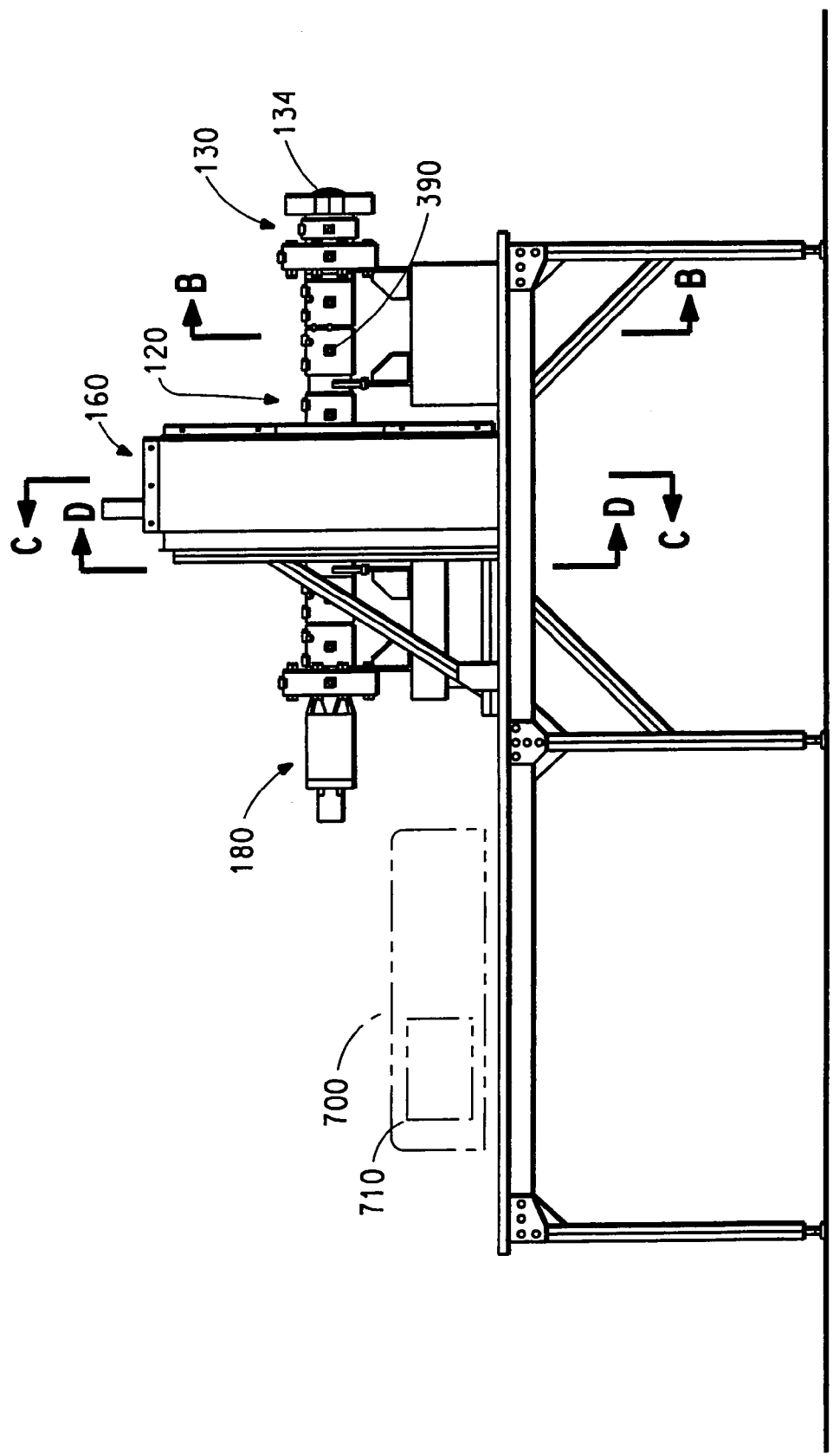
FIG. 3 is an elevation view of the apparatus.
Figure 4:
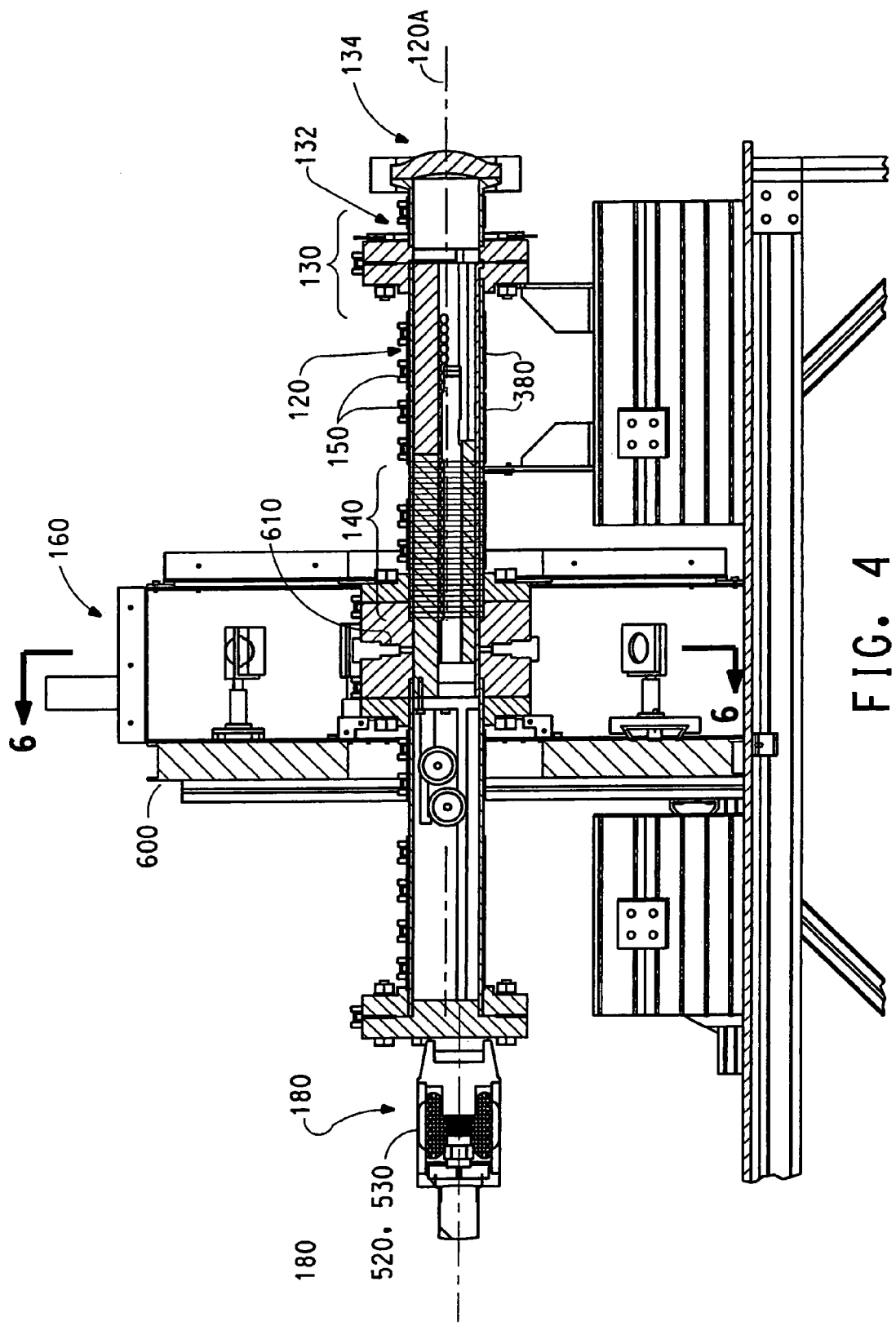
FIG. 4 is a sectional elevation view of the apparatus, taken along section lines 4-4 of FIG. 2.

FIG. 2 is a perspective view of the reaction apparatus 100 showing a generally cylindrical housing 120, an analytical monitoring section 160, and an attached a drive section 180. FIGS. 3 and 4 are side elevation views of the reaction apparatus 100 showing the cylindrical housing 120, which contains a loading/unloading section 130 having an airlock 132 and a cover 134; a reaction section 140; a distribution manifold system 150; an analytical monitoring section 160; and an attached a drive section 180.

Figure 7:
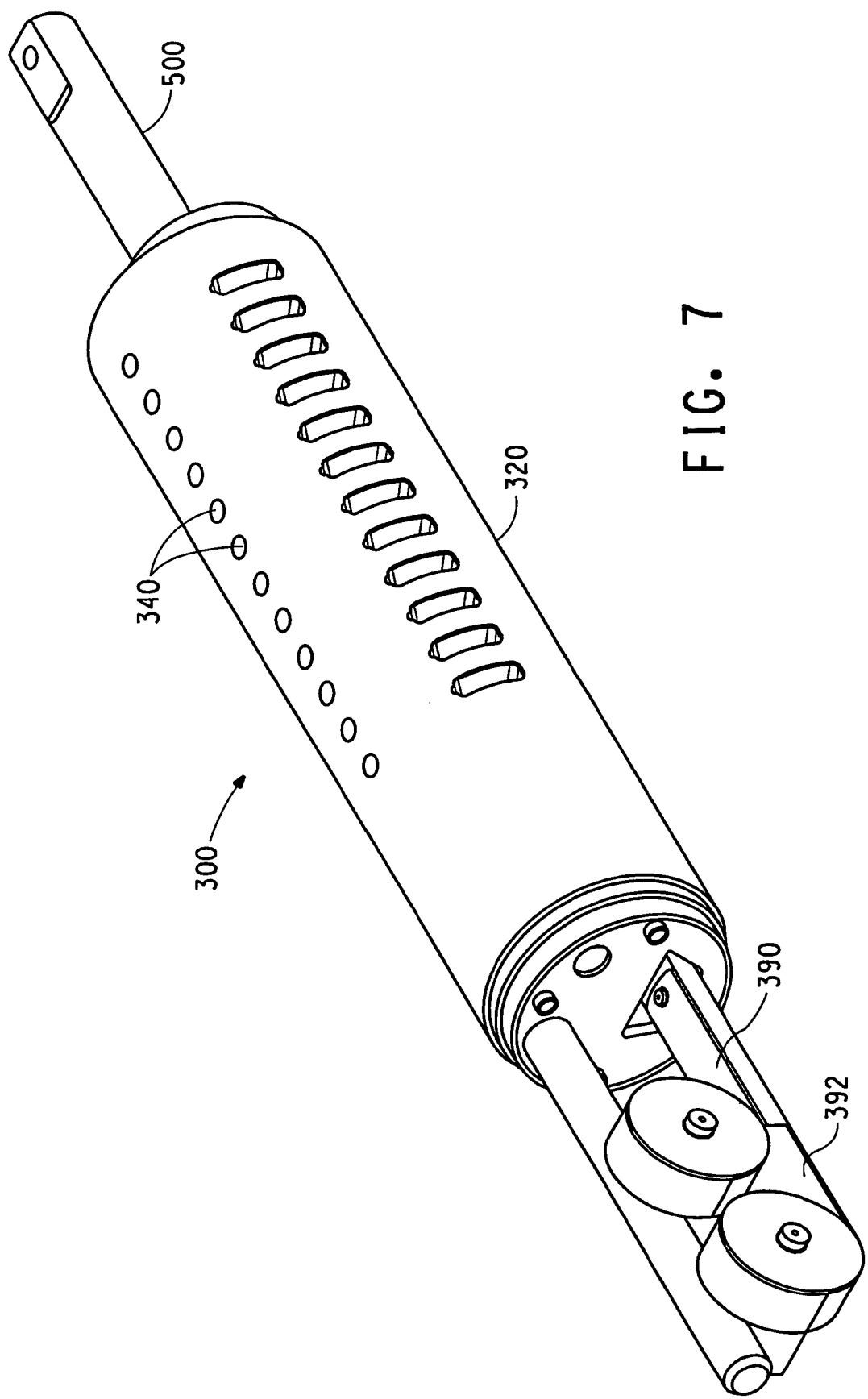
FIG. 7 is a first perspective view of the reaction assembly.
Figure 8:
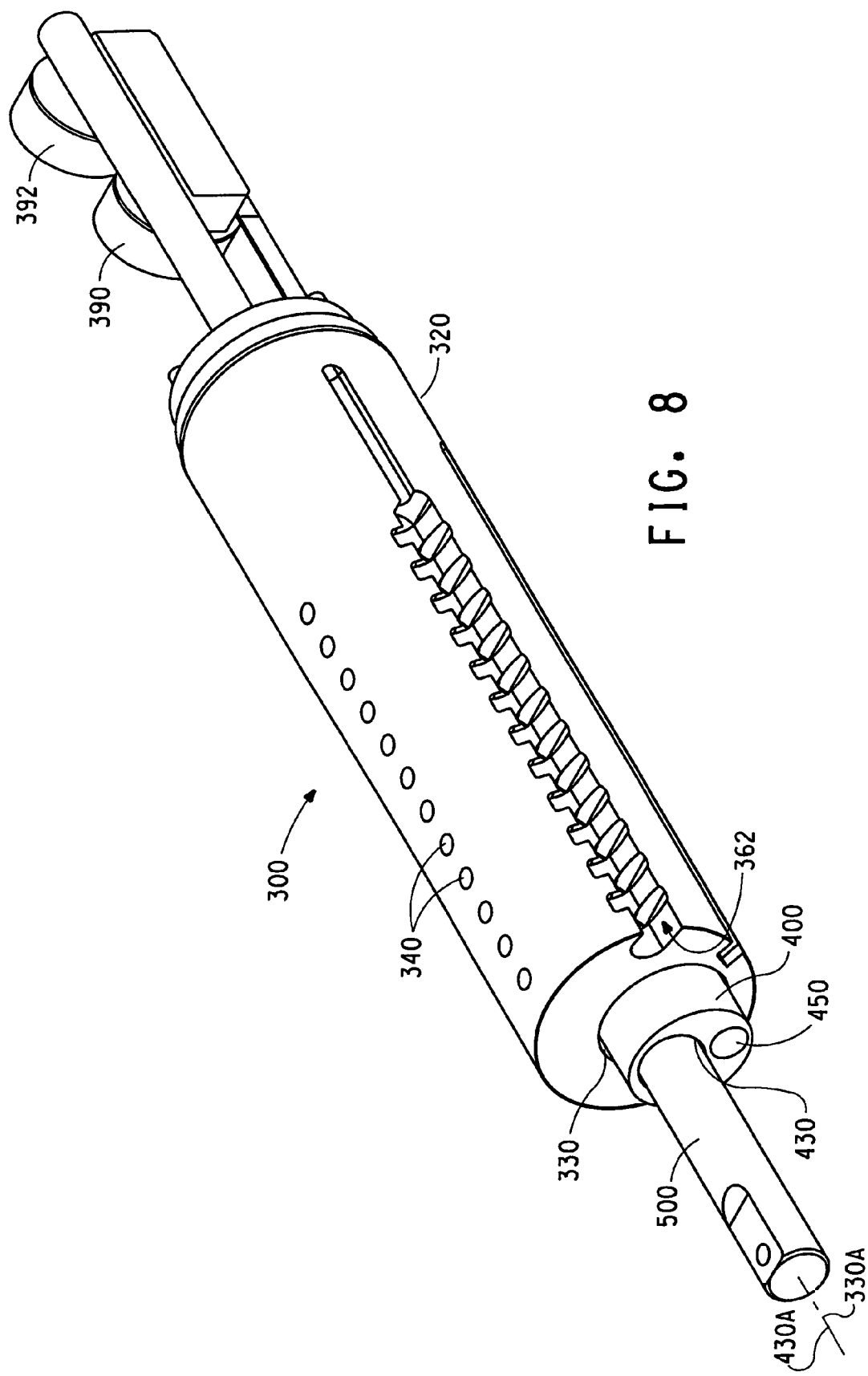
FIG. 8 is a second perspective view, opposite the view of FIG. 7, of the reaction assembly.

As seen in the perspective views of FIGS. 7 and 8 and sectional views 9 and 10, a reactor assembly 300 is shown, assembly 300 being contained within the housing 120, and being movable in a direction along the axis 120A of housing 120.

Figure 9:
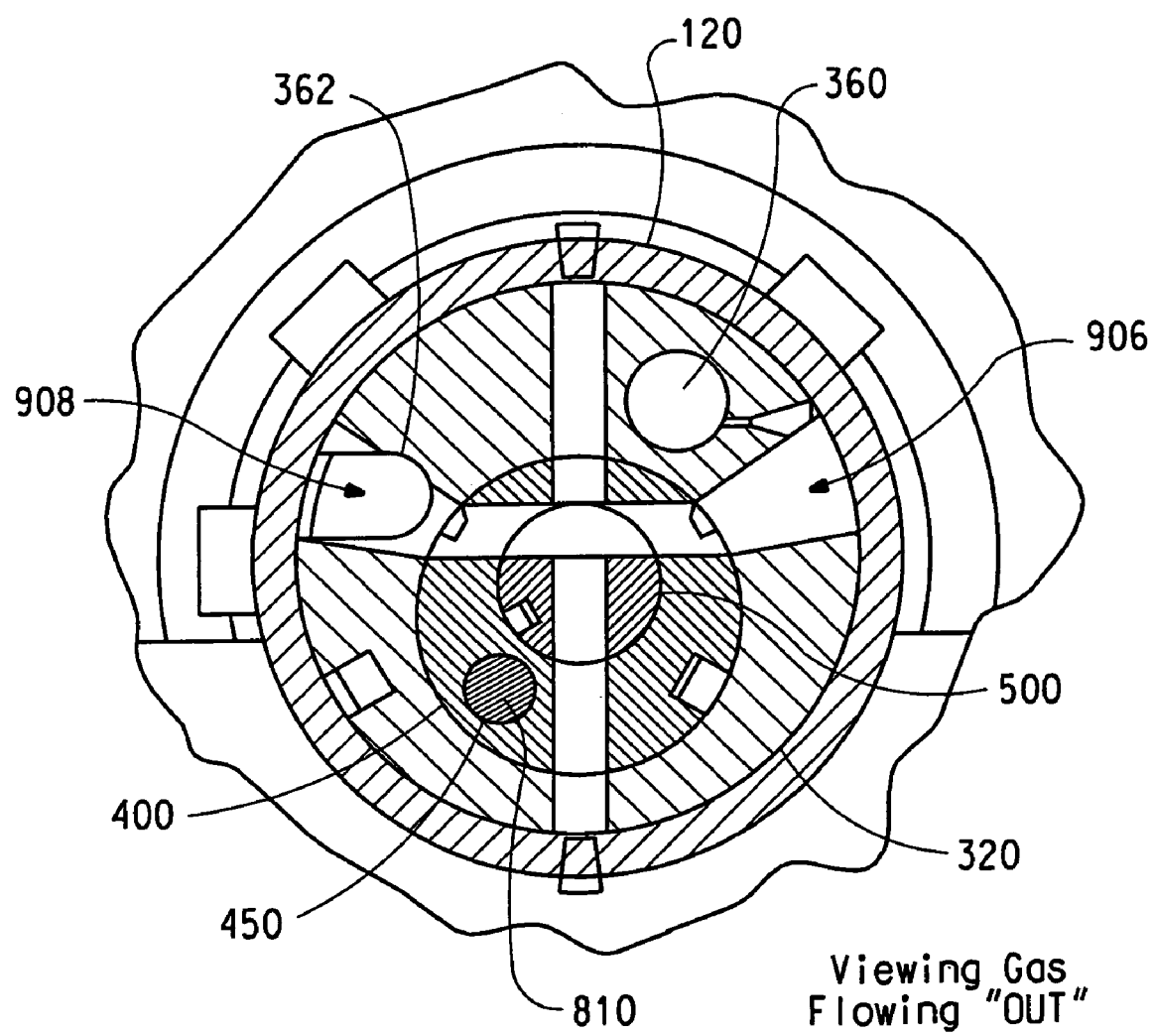
FIG. 9 is a first sectional view of the reaction assembly.
Figure 10:
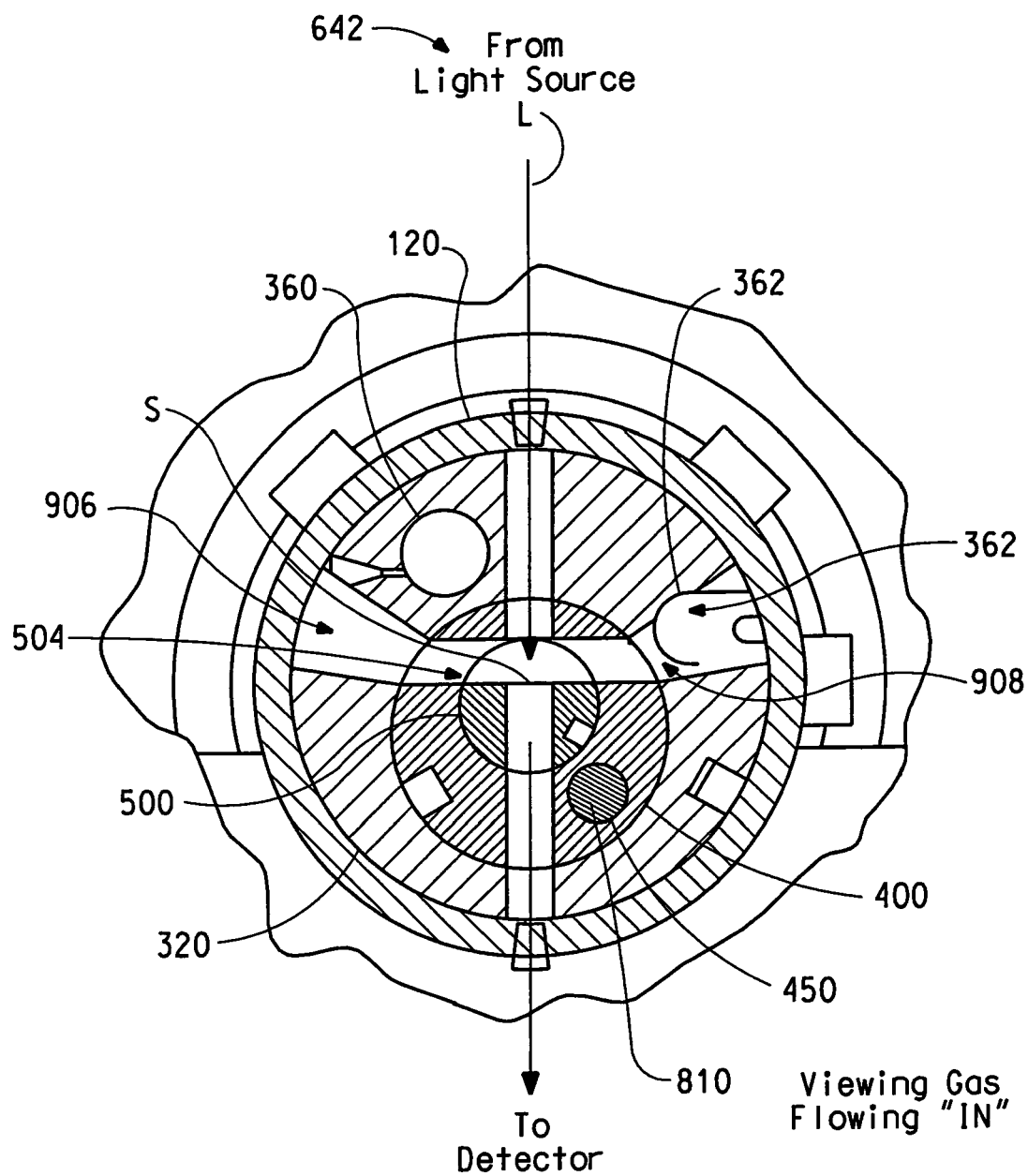
FIG. 10 is a second sectional view of the reaction assembly.

The reactor assembly contains a cylindrical outer body 320 having a generally cylindrical bore 330 having an axis 330A and a plurality of ports 340. As seen in FIGS. 3 and 4, the apparatus also contains heating elements 380, which may be one or more band heaters clamped around the reactor housing; and associated temperature sensing elements 390. As shown in FIGS. 9 and 10, the outer body 320 contains a fluid distribution manifold 360. Bore 330 receives a slidable cylindrical inner body 400. A pair of constant tension springs 390, 392 bias the cylindrical outer body 320 and the cylindrical inner body 400 against the threaded drive screw 810. In an alternative embodiment, instead of using tension springs 390, 392, outer body 320, inner body 400 and sample holder 500 may all be made slidable in and out both ends of reactor assembly 300.

Figure 11:
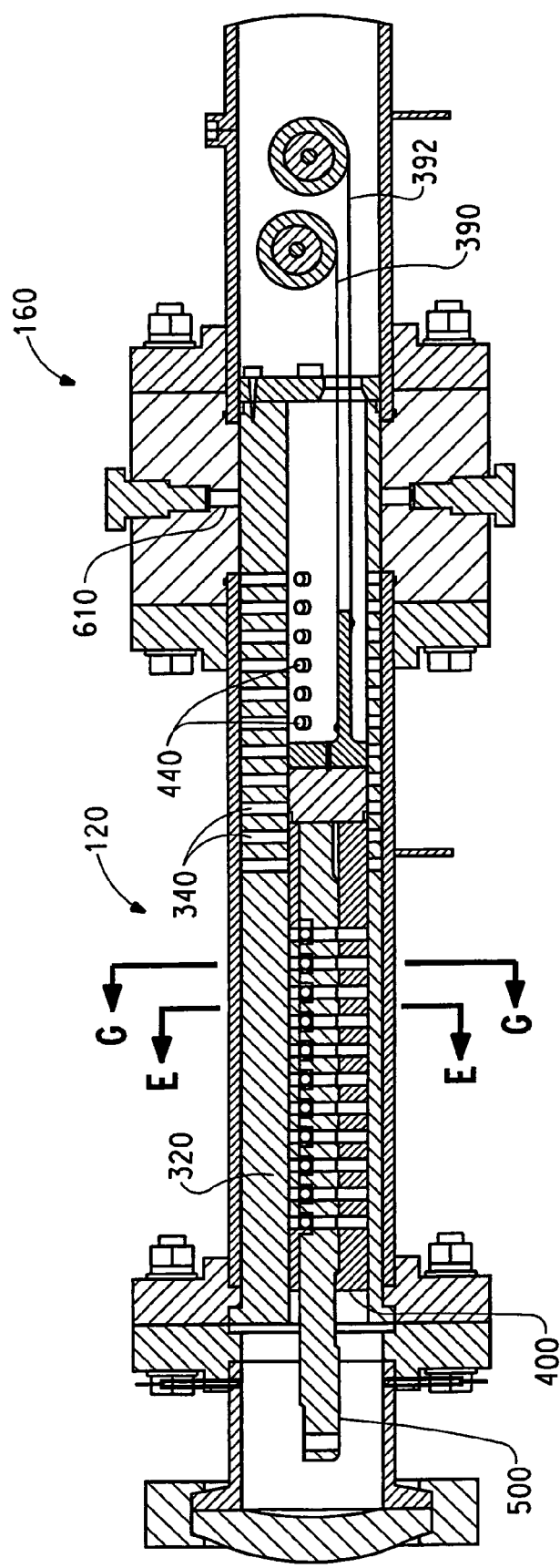
FIG. 11 is a sectional partial view of the apparatus, taken along section lines 4-4 of FIG. 2, showing the sample holder in the loading/unloading position.
Figure 12:
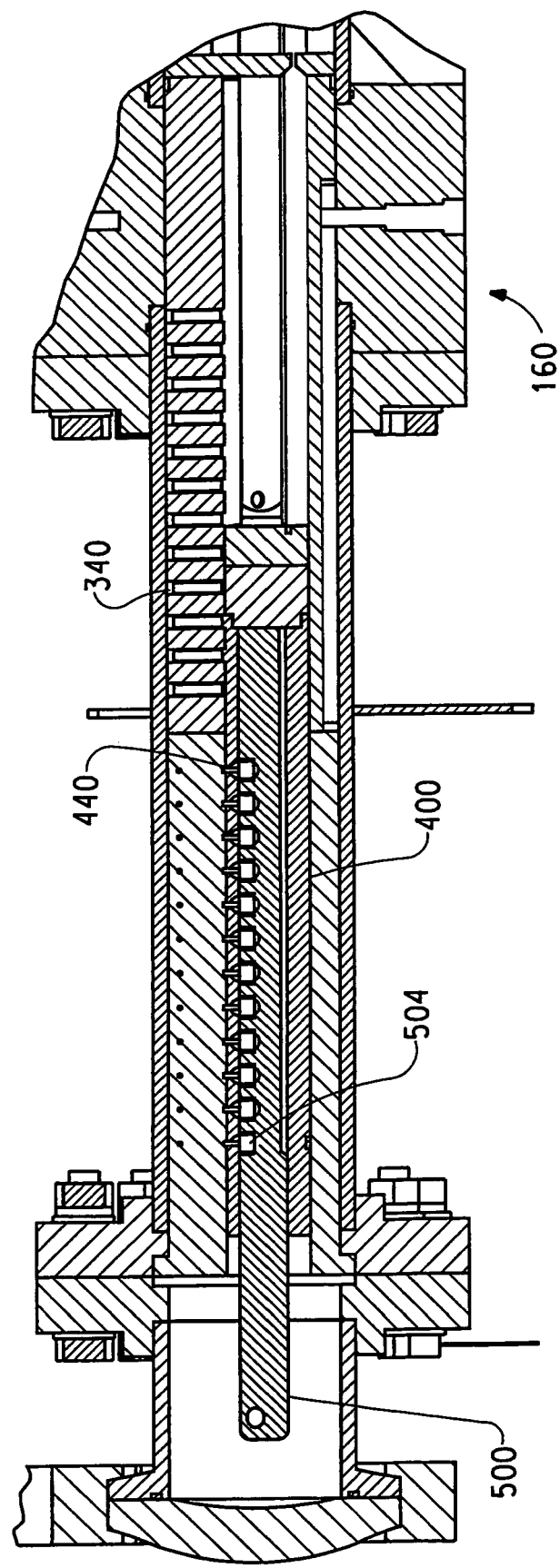
FIG. 12 is an enlarged sectional view of the apparatus, enlarging a portion of FIG. 11.
Figure 13:
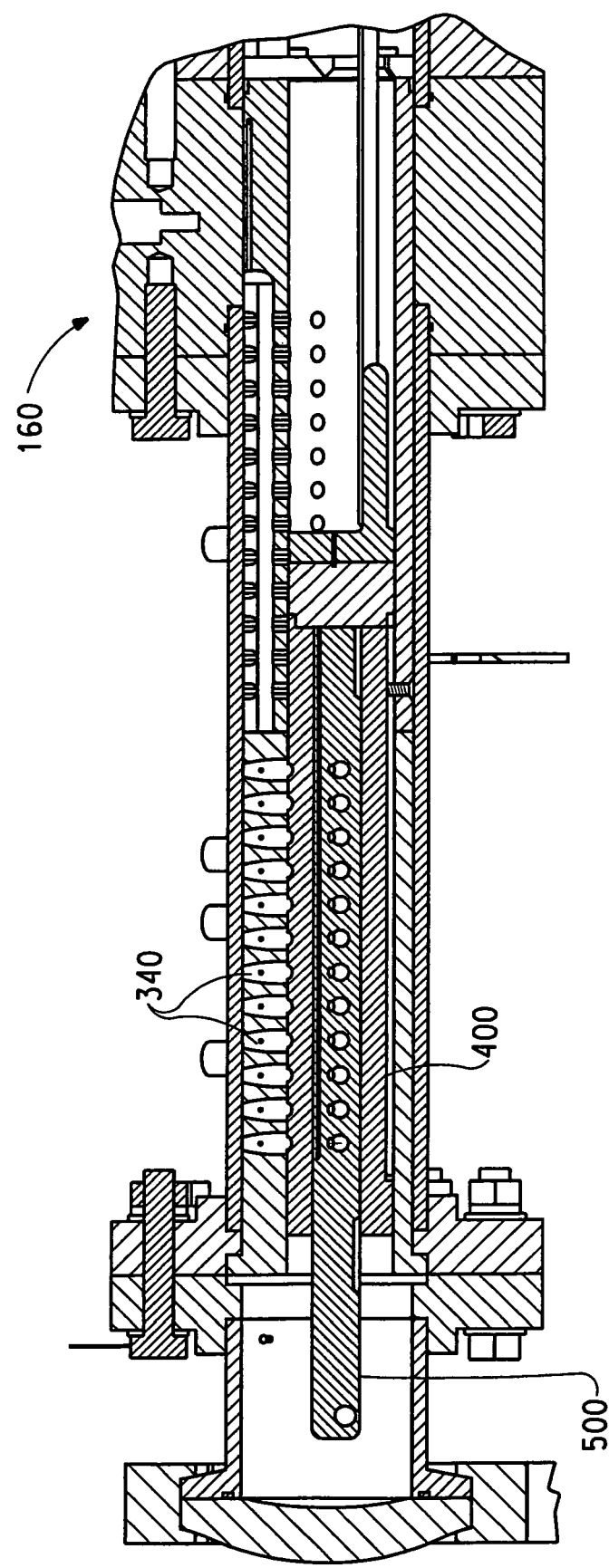
FIG. 13 is a sectional view of the apparatus, taken along section lines K-K of FIG. 6.
Figure 16A:
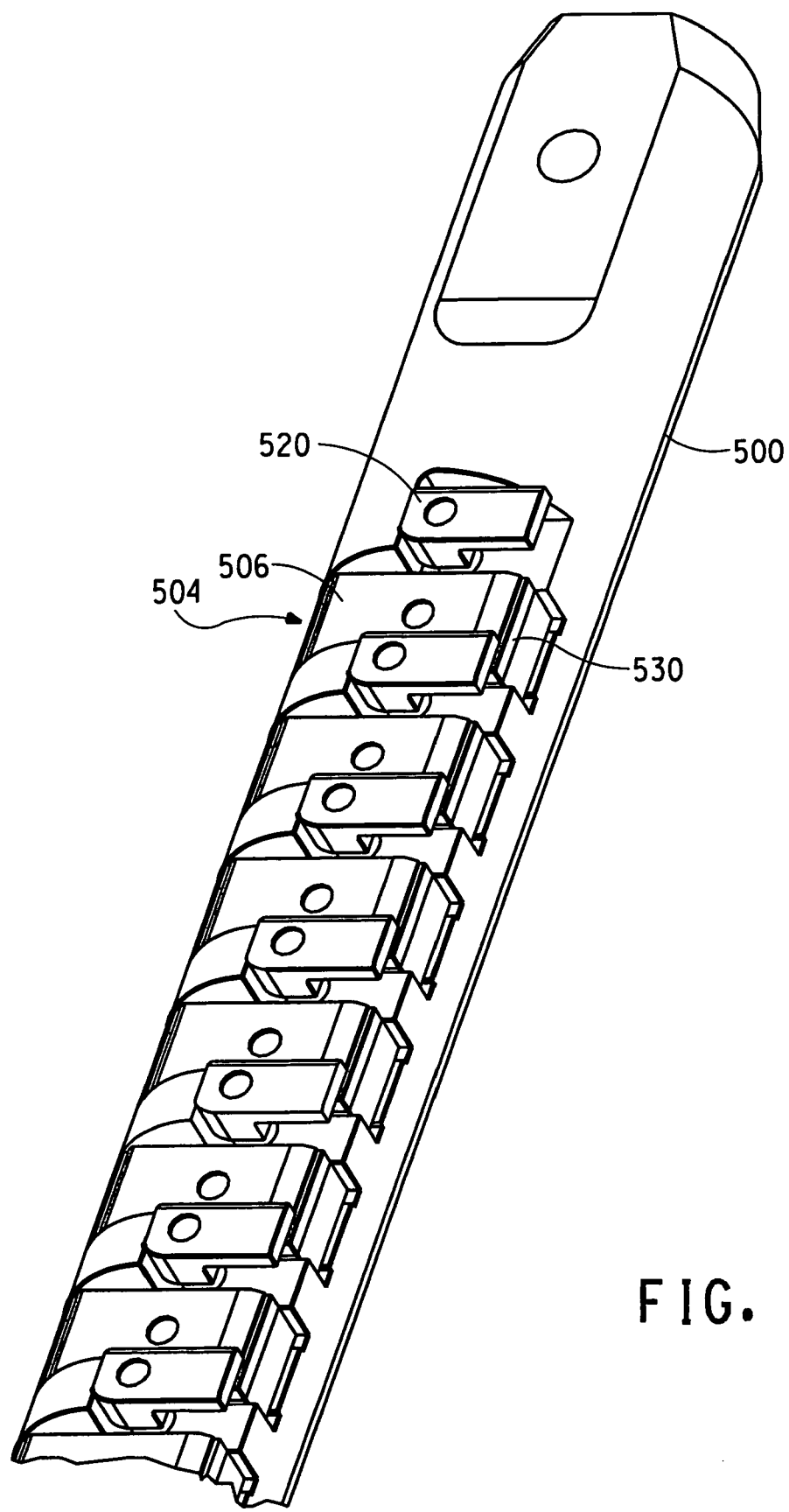
FIG. 16A is an enlarged view of a second sample holder having a sample hold-down clamp, the clamp being in a release position.
Figure 16B:
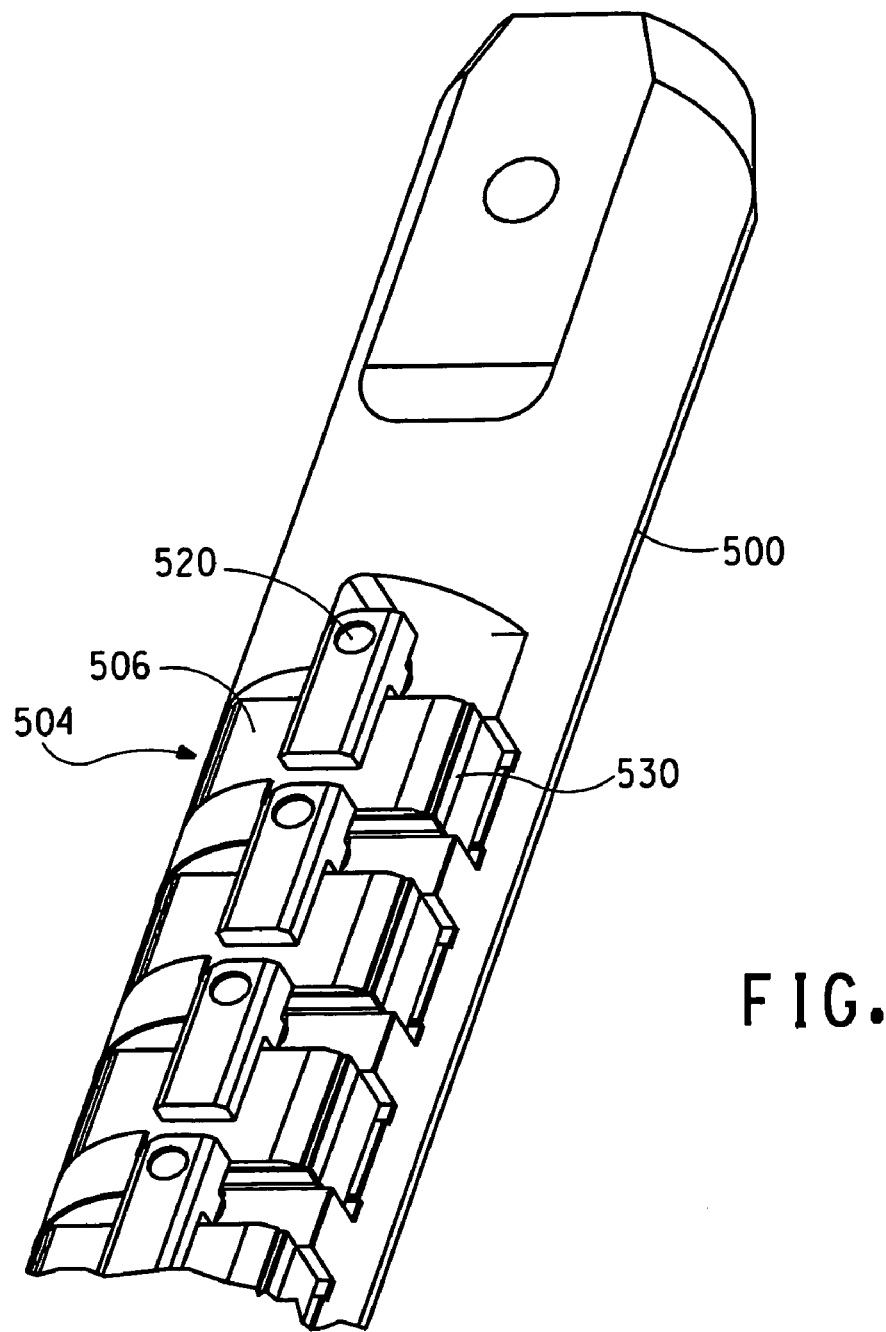
FIG. 16B is a view of the second sample holder showing the sample hold-down clamp rotated to the holding position with the clamp in the up position.
Figure 16C:
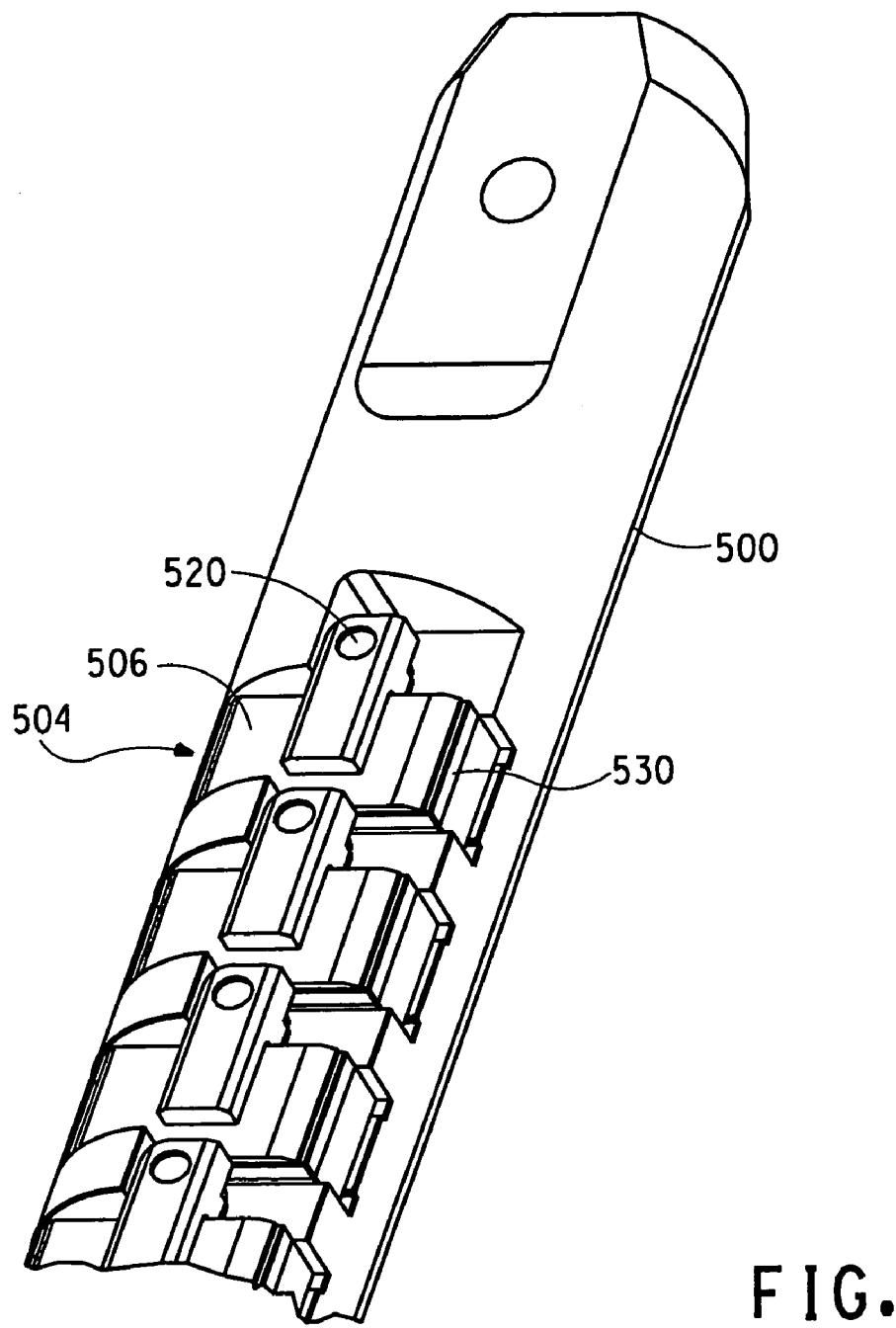
FIG. 16C is a view of the second sample holder showing the sample hold-down clamp rotated to the holding position with the clamp in the down position.
Figure 17:
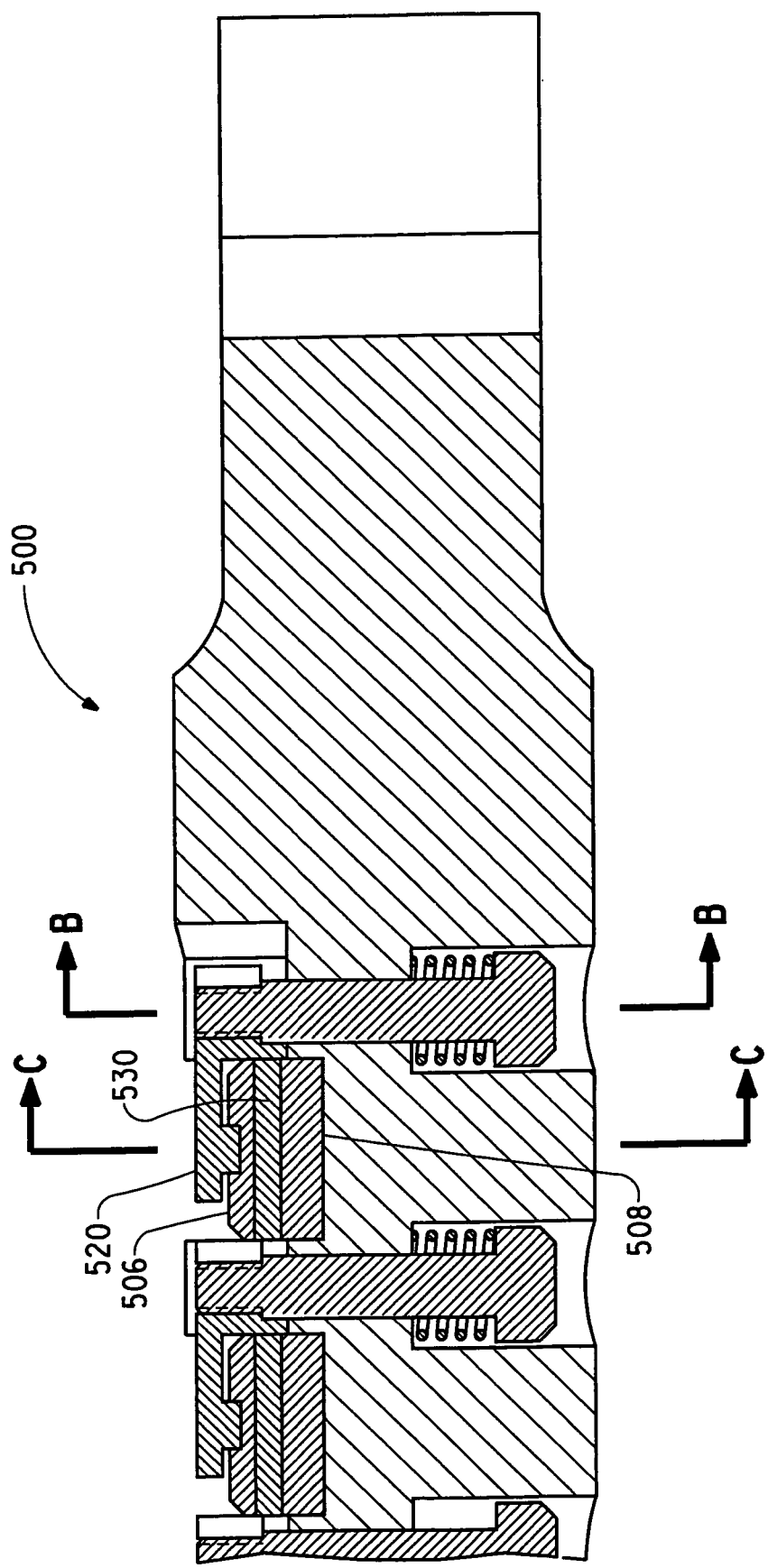
FIG. 17 is a sectional view, taken along section lines 17-17 of FIG. 16C.

The inner body 400 has a generally cylindrical first bore 430 having an axis 430, which is coincident with axis 330A, and a plurality of ports 440 (as shown in FIGS. 11 and 12). First bore 430 receives slidable sample holder 500. The inner body 400 has a threaded second bore 450 that engages a threaded drive screw 810 (as shown in FIG. 1) of the 30 positioning system 30. As shown in FIGS. 16A-16C, sample holder 500 has a plurality of reaction sample holding positions 504 for containing the samples to be reacted.

Figure 14:
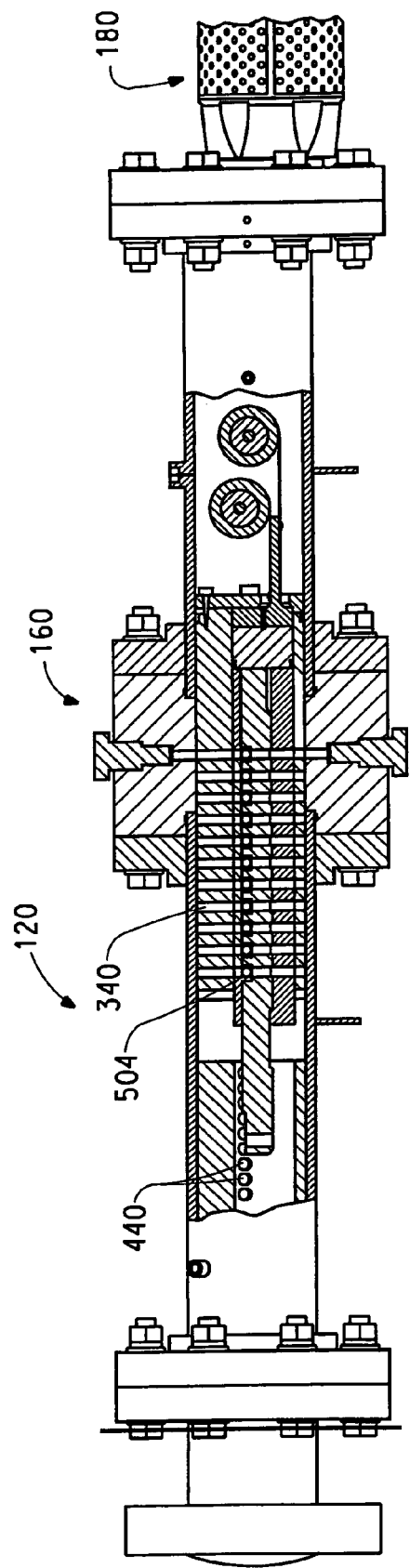
FIG. 14 is a view, partially in section, showing the sample holder in an optical measurement position.
Figure 15:
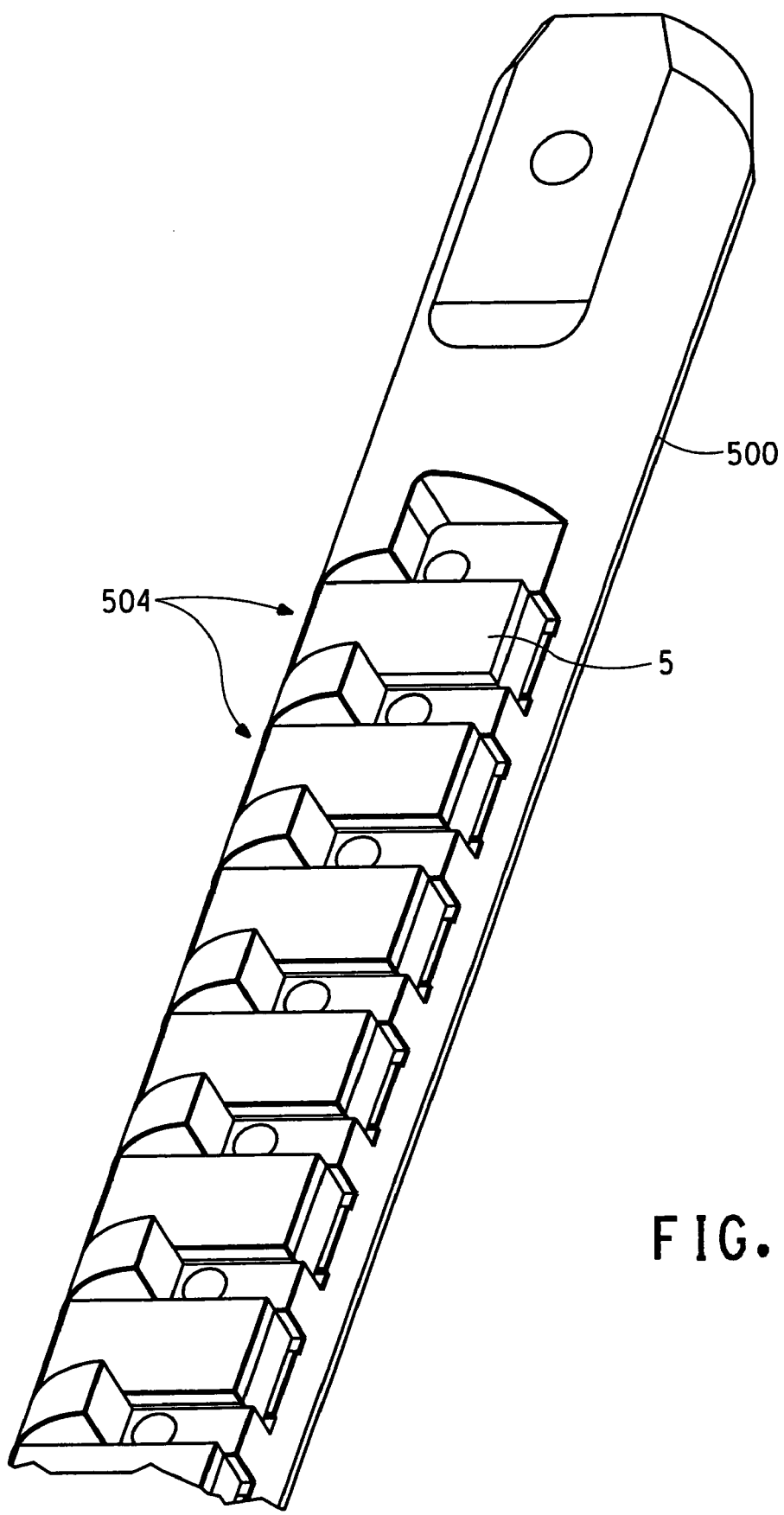
FIG. 15 is an enlarged view of a first embodiment of the sample holder.

Referring again to FIGS. 7 and 8, the sample holder 500 is slidable along the axis 430A to a fully inserted position with the inner body 400. When the sample holder 500 is in the fully inserted position within the inner body 400, as seen in the sectional view of FIG. 14, each of the plurality of sample holding positions 504 is aligned with each of the plurality of ports 340 of the outer body 320.

As shown in FIG. 1, the position control system 30 comprises the threaded screw 810, a drive motor 820 (such as a stepper motor) and associated reduction gears 830, a drive screw position encoder 840 and a drive controller 850 interfaced to the system controller 20.

When the ports 440 of the inner body 400 are aligned with the ports 340 of the outer body 320, a gas inlet passage 906 from the inlet distribution manifold to each sample holding position 504 is established; and a gas outlet passage 908 from each sample holding position 504 to the exhaust manifold 362 is established. This can be seen in sectional views FIGS. 9 and 10.

Figure 5:
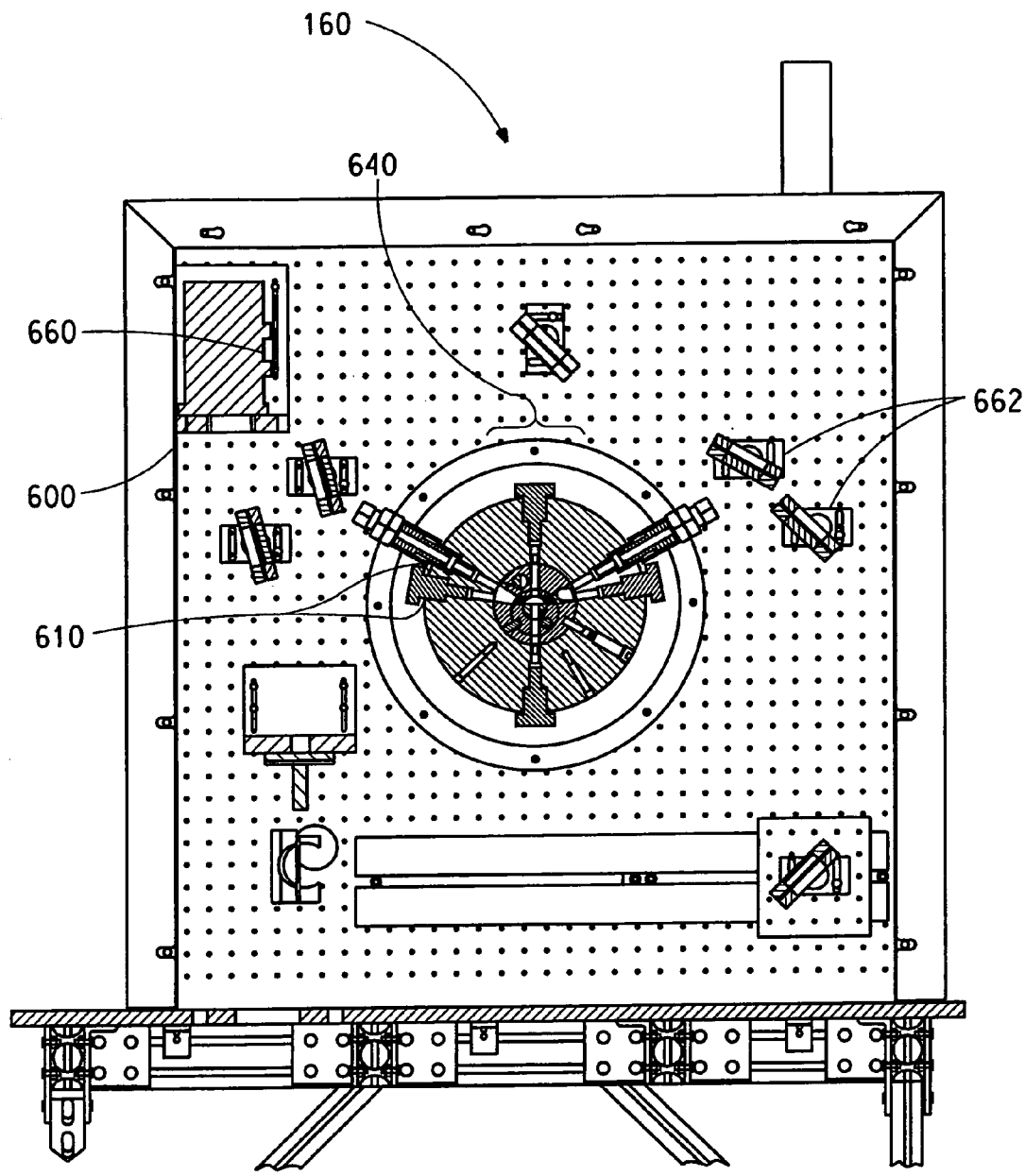
FIG. 5 is a sectional view taken along section lines C-C of FIG. 3.
Figure 6:
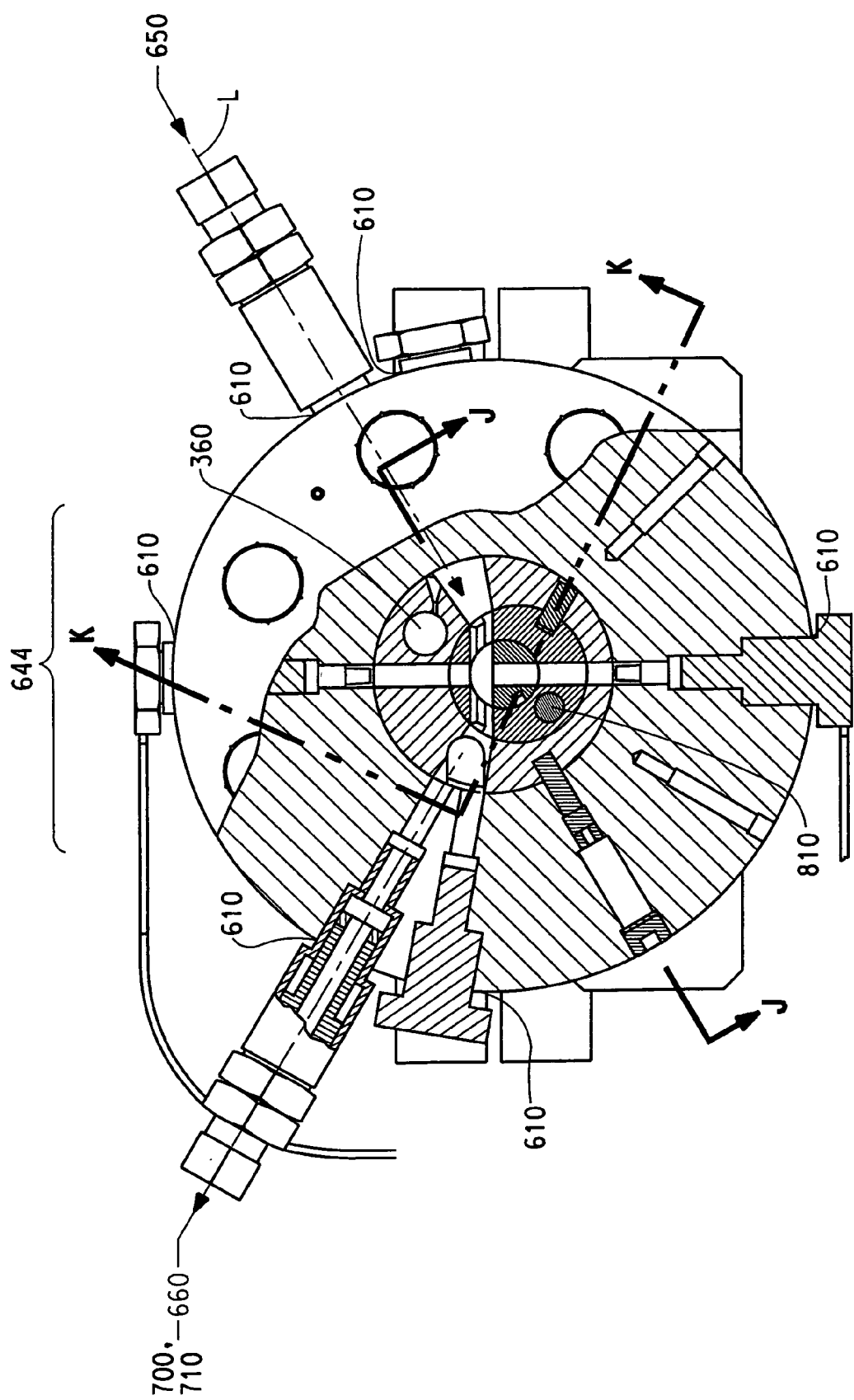
FIG. 6 is a partial sectional view taken along section lines C-C of FIG. 3.

An example of one type of the analytical monitoring section 160 is the optical monitoring section seen in FIGS. 4, 5 and 6. It comprises a base assembly 600, at least one analytical ports (such as an optical port) 610, and at least one optical arrangement 640 (i.e. the necessary equipment, commands and activating resources for the particular type of optical analysis), such as a paired optical source 650 and detector 660 and an associated spectrometer 700 or 710. In the optical analysis, light may be passed from the optical source 650 to the optical detector 660 by reflection off of mirrors 662.

An optical arrangement 640 may, for example, be implemented using a spectrometer 700 (as shown in FIG. 3) being capable of performing a measurement at ultraviolet or visible wavelengths of a sample contained on a sample holder positioned within a sample holding position 504 to characterize the sample. Alternatively a spectrometer 710 (also shown in FIG. 3) capable of performing a measurement at infrared wavelengths may be used to characterize the sample. The specific optical arrangement to be utilized is selected according to the characteristics of the sample. An optical transmission measurement 642, as shown in FIG. 10, may be employed for samples that are at least partially transparent. An optical reflection arrangement 644, as shown in FIG. 6, may be employed for samples that are opaque.

Figure 18:
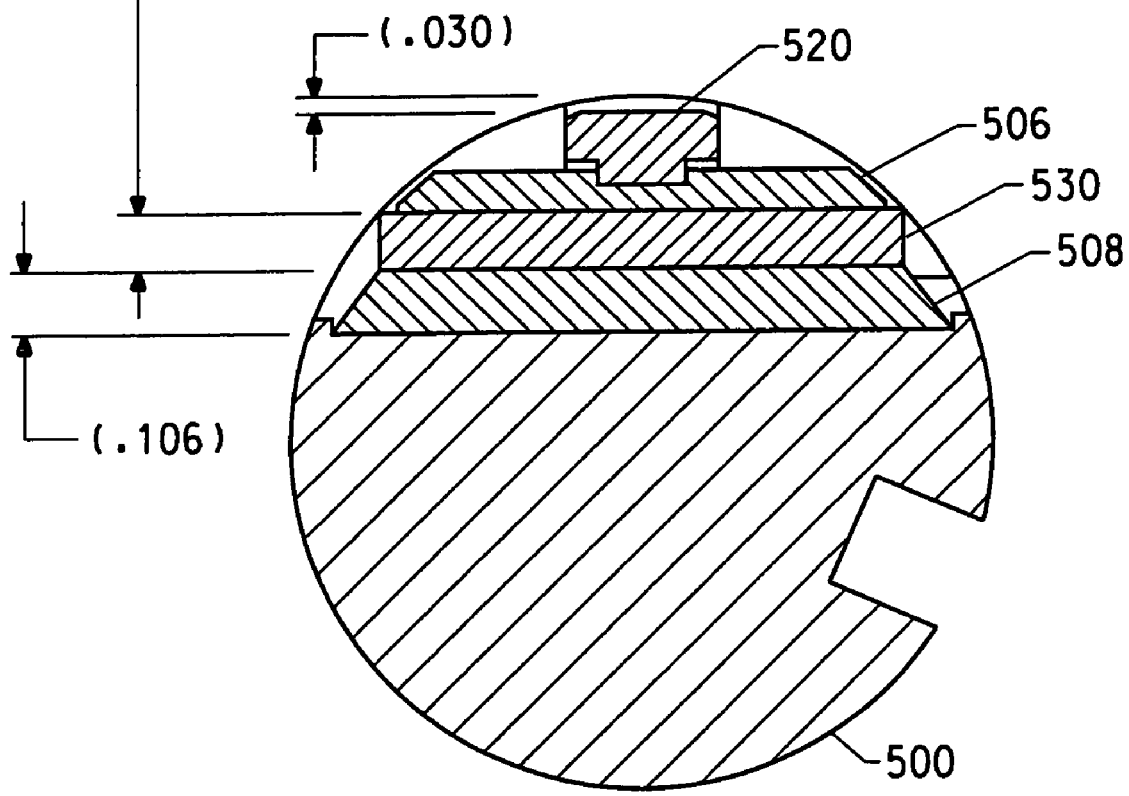
FIG. 18 is a sectional view, taken along section lines 18-18 of FIG. 16C, showing an attenuated total internal reflection (ATR) measurement arrangement.
Figure 18A:
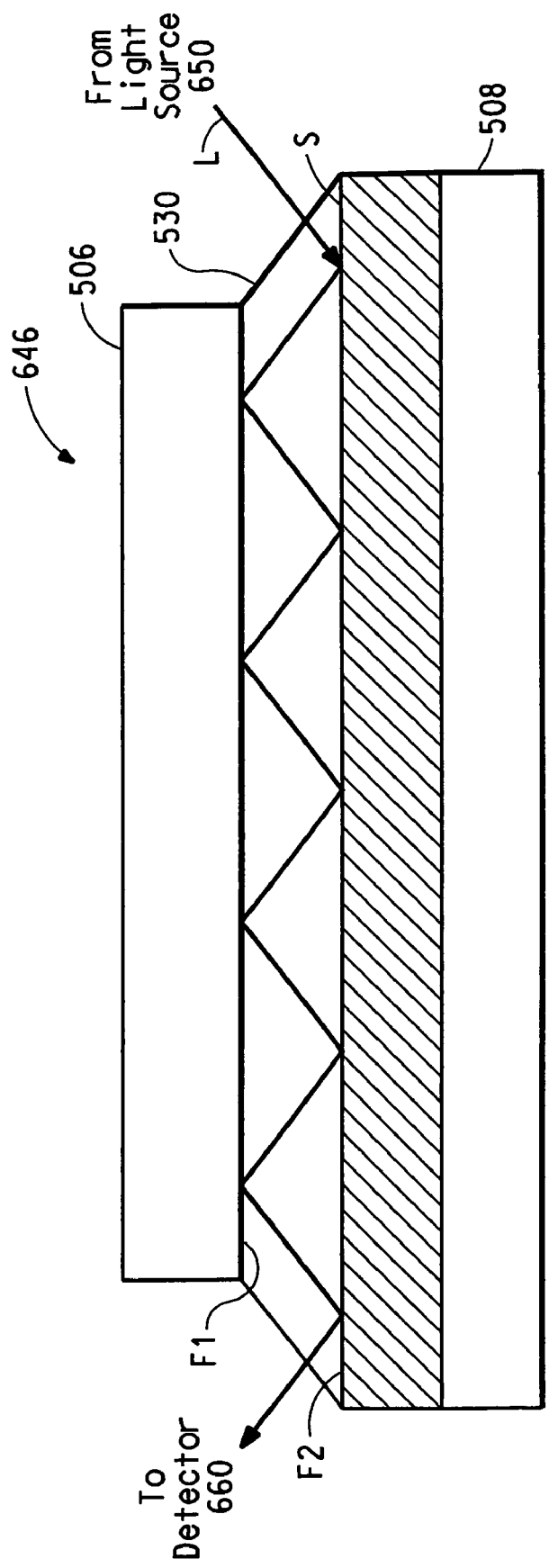
FIG. 18A is an enlarged sectional view showing the interaction of light with the sample in the ATR measurement arrangement.

In one embodiment, an attenuated total internal reflection (ATR) arrangement 646, as shown in FIG. 18A, may be employed for surface measurements of a sample S. The sample S is fixed either on the top or bottom by a rigid light conducting Attenuated, Total Reflection (ATR) transparent optical cover 530 such as a crystal. This assembly may be fixed by rigid supports 506, 508 on the top and bottom of the ATR crystal. The ATR crystal cross-section is preferred to be a trapezoid. Light L enters the ATR crystal normal to one of the end faces to make an angle of reflection with the faces F1, F2 that results in a total internal reflection condition. At each reflection there is emitted an evanescent standing wave, which decays exponentially with distance from the crystal interface into any material which is contacted with the ATR crystal surface. In FIG. 18A, the top of the sample S is monitored within the evanescent waves at each reflection which transmit into the sample S. As the sample absorbs amounts of light within the evanescent waves, the absorption can be detected from the light leaving the ATR crystal by a light detector.

Other types of analysis that may be used instead of, or in addition to, optical analysis include analysis selected from the group consisting of ultrasonic, electrostatic, magnetic, radio frequency or x-ray analysis.

In operation, the system 10 is capable of performing a plurality of chemical reactions. First, the sample holder 500 is loaded with samples to be reacted. When optical analysis, such as an ATR measurement, is to be made, a hold-down clamp 520, as shown in FIG. 16A, is positioned in the release position so that a sample and the support 508 can be inserted into the sample holding position 504. The sample S, mounted on support 508, is inserted into the sample holding position 504, and a transparent optical cover 530 is placed over support 508, and top support 506 is placed over cover 530. The clamp 520 is rotated to the holding position with the clamp in the up position, as shown in FIG. 16B. Then the clamp 520 is moved to the down position to hold the cover 530 tightly against top support 506, sealing the sample S in the sample holding position 504, as shown in FIGS. 16C and 18A. The sample holder 500 is inserted into the bore 430 of cylindrical inner body 400 of the reactor assembly 300 when the reactor assembly and the inner body are both positioned at an undocked position.

The cylindrical inner body 400 of the reactor assembly 300 is then moved to a docked position within the outer body 320 by the positioning control unit 30. At this time, the controller 20 may command the temperature control system 60 to bring the interior of outer body 320 to a predetermined temperature if necessary. The temperature control system 60 in such event energizes heating elements 380, and temperature-sensing elements 390 provide a feedback signal to the temperature control system 60. If pressure other than ambient is to be used, the control computer 20 commands the pressure control system 80 to either raise or lower the pressure within the apparatus to the desired pressure. Conventional pressure transducers (not shown) provide a pressure feedback signal to the pressure control system 80.

Next the controller 20 causes the fluid distribution system 40 to introduce one or more reactant fluid(s), such as gas(es) and/or liquid(s), to the samples within the sample holding positions 504, and the reactant fluid(s) react with the sample. When the reaction is complete, the positioning control unit 30 sequentially positions and re-positions the reactor assembly 300 so that each of the sample holding positions 504 is individually aligned with the analytical monitoring section 160. The sample holding positions can be positioned for individual alignment with the analytical monitoring section 160 in any order and more than once.

As each sample holding position 504 is brought slidably into its individual alignment with analytical port 610, at least one analytical measurement is made of that sample. Upon completion of the analytical measurements, the reactor assembly 300 is returned to the initial position adjacent the load/unload section 130. At this time the temperature and pressure within the apparatus is returned to ambient, if necessary. This may be facilitated by flushing the reaction assembly to quench the reaction, such as with an inert gas at ambient temperature and pressure. When the desired conditions have been reached, the inner body 400 of the reactor assembly 300 is moved to the undocked position, the cover 134 is removed and the sample holder 500 is removed from the reactor assembly 300.

In various alternative embodiments, the invention provides a method for testing a plurality of samples, by (a) simultaneously reacting all samples with a fluid, and (b) during or after the reaction of the samples with the fluid, subjecting each sample in sequence to analysis. Once the airlock 132 is closed, the reaction of the samples with the fluid and the analysis are performed in a sealed vessel. While the samples remain in the sealed vessel, it is possible, if desired, to subjecting one or more of them to a second simultaneous reaction with a fluid, and a second analysis, and this sequence of steps may be repeated as many times as desired.

Each sample holding position 504 of the sample holder 500 provides a chamber in which the temperature or the pressure is controlled when the sample in that position is reacted. Each such reaction chamber is isolated from the reaction chamber provided by each other sample holding position. The isolation is provided by the fact that the sample holder 500 is slidable within the inner body 400, and the inner body is slidable with in the outer body 320. At any sample holding position at which there is a corresponding port in the inner body, when the inner body is moved such that the port in the inner body is aligned with the port in the outer body, the sample is exposed to the fluid in the manifold of the outer body. A reaction chamber exists, for example, when a port in both the outer and inner bodies are lined up with a sample holding position, and the ports have access to a fluid distribution manifold. That sample holding position is, however, isolated from all other sample holding positions and from the analytical port by the annulus of the outer body and the annulus of the inner body. The invention thus provides a method in which the chamber in which each samples is exposed to or reacted with the fluid is isolated from the chamber in which each samples is subjected to analysis.

The analysis may be performed during, or after completion of, the reaction of the samples with the fluid.

In one segment of the reaction apparatus, when the ports in the inner body are aligned with the ports of the outer body, all sample holding positions are exposed to the fluid in the manifold, which may be a reactive or non-reactive fluid. In this segment, it is thus possible to simultaneously expose all samples to or react all samples with, the fluid. In another optional segment of the apparatus, however, a port in the inner body is not available for alignment with each port in the outer body. In this segment, it is thus possible to simultaneously expose one or more members of a subgroup of the samples to, or react one or more member of the subgroup with, the fluid. A subgroup of the group of samples in the sample holder is a number of samples that is less than the number in the whole group. The number in the subgroup may be one, or any other number that is less than the number in the whole group. The step of exposing or reacting the subgroup may be performed before or after the step of exposing or reacting the whole group.

The samples may be brought to a predetermined temperature in a segment or chamber of the reaction vessel before the sample holding positions in the sample holder have been placed in alignment with the ports in the outer body. The exposure or reaction of the samples may thus be conducted in a chamber of the apparatus that is isolated from a temperature-adjustment chamber by the sliding motion of the sample holder moving into alignment with the ports in the outer body. When the sample holder is positioned in that alignment, moving the inner body such that its ports are also in the same alignment exposes the samples to the fluid in the manifold. After completion of reaction and analysis, the sample holder can be returned to the former position at which time the temperature of all samples can be further adjusted to a temperature above or below the predetermined temperature. In similar fashion, the samples may be exposed to a non-reactive fluid in a different segment of the apparatus from that in which they are exposed to a reactive fluid.

As mentioned above, the samples are placed in position to receive exposure to a fluid when the sample holding positions are placed in alignment with the ports in the outer body. Then by sliding the inner body component of the apparatus relative to the outer body component, an inlet passage is created for the fluid to flow from the manifold into the area of the sample holding position. In this sense, the inner body forms a cover for the sample holder with the result that the cover can be open when the ports of the inner body are in alignment with the ports of the outer body, and can be closed when the ports are not in alignment. When the sample holder is later moved into alignment with the analytical port, the sample holding position remains isolated by the annulus of the inner body from the reaction chamber previously formed when the respective ports of the inner and outer bodies were in alignment directly over the sample holding position.

After removal of the sample holder 500 from the reaction vessel, the sample hold-down clamp 520, if used, is released from down holding position to the up position (FIG. 16C), and then the clamp may be rotated to the sample release position (FIG. 16B) and the in the up position (FIG. 16A).

FIGS. 19 through 26 depict, in block diagram form, software for controlling the system 10. FIG. 19 is a block diagram showing a main control routine for controlling the computer controller. FIG. 20 is a block diagram showing a routine for controlling a spectrometer when the analytical method employed is an optical measurement system. FIG. 21 shows a routine for recording parameters and settings. FIG. 22 shows a routine for configuring elements of the system. FIG. 23 depicts a routine for controlling valves and displaying set-points. FIG. 24 shows a routine for recording parameters and experimental data. FIG. 25 depicts a routine for displaying spectral data when the analytical method employed is an optical measurement system. FIG. 26 shows a routine for controlling the positioning system.

In operation, the system 10 is controlled by software that utilizes a graphical user interface to enable the user to operate the reaction apparatus 100 in an automated manner. The user is enabled to program all process, measurement and analysis parameters before the experiment is initiated. This programming is divided into three main stages: Set-Up, Experiment and Analysis.

In the Set-Up Stage, the user selects all process and measurement parameters. Process parameters include all temperature set-points for the temperature control system 60 for the loading, reactor and unloading sections; vacuum or pressure level for the pressure control system 80; motor drive controller parameters such as movement velocity; hold times for loading, preheat and unloading quench gas flows; as well as activation schedule to the fluid distribution system 40 for the solenoid-actuated valves which handle the loading-preheat fluid and unloading-quench fluid. When the analytical method employed is an optical measurement system, the measurement parameters may include, for example, spectroscopy specifications for a UV/Visible spectrometer 700 and FTIR 710; identification of which sample positions 504 to measure; any desired delay time between sampling cycles; the total number of sampling cycles; and data storage path. All of these parameters completely define the experiment, and are recorded in a separate method file. The method file allows the user to document the experiment in a laboratory record, and may also be used as a template for future experiments.

The Set-Up Stage parameters are selected by the user by clicking on a "Set-Up" control button. This action makes available several additional control buttons that access different classes of experimental parameters. For example, a "Set Points" control button displays a window in which the user enters all temperature set points. A "Data Path" control button displays a window that allows the user to either define or specify an existing file system directory or create a new file system directory in which to store the experimental data files. A "Motor Sampling" button displays a window that permits the user to calibrate the motor 820, specify active sampling positions during the experiment, as well as report motion data from the drive controller 850. When the analytical method employed is an optical measurement system, a button such as an "Ocean Optics" button displays a window that permits the user to specify UV/Vis spectroscopy parameters for a spectrometer, such as an Ocean Optics spectrometer 700. A button such as a "Nicolet" button displays a window that permits the user to specify FTIR spectroscopy parameters for a spectrometer such as a Nicolet spectrometer 710.

A "Parameters" button displays a window that permits the user to program the experimental method and sequence. The experimental method comprises sections entitled "Start", "Sampling" and "End". Each of these sections is optional and may be selected as either active or bypassed during the experiment. If the user activates the Start section, then the user may specify loading zone temperatures, loading fluid treatment flows and exposure time. If the user activates the Sampling section, the user may specify the number of sampling cycles, sampling kinetics as well as any delay time between sampling cycles. Furthermore, the user may specify the unloading temperature in advance of the End section so that the temperature may be adjusted by the temperature controllers during the experiment.

There are two types of sampling kinetics. In linear sampling kinetics, the user specifies a constant delay time between sampling cycles, which is maintained over all sampling cycles. In logarithmic sampling kinetics, the user specifies an initial delay time between sampling cycles. Here the delay time is kept constant for ten sampling cycles, and then doubled for the next ten sampling cycles. This process repeats until all specified sampling cycles have been followed. The logarithmic kinetics specification is ideal for reactions that are fast in the beginning, become progressively slower but ultimately last for long periods of time. Thus an optimal amount of data are collected and stored for the user to analyze. If the user activates the End section, the user may specify the unloading zone temperatures, unloading-quench gas treatment flows and exposure times.

In the Experiment Stage the user initiates the programmed instructions set in the Set-Up stage. Here the computer autonomously operates the reactor, and controls the process environment and data collection without further presence required of the user. The software does provide the user the capability to pause and restart as well as to abort the experiment should such actions be required. The Experiment Stage is accessed by the user in the software by clicking on an "Experiment" control button in the graphical user interface.

In the Analysis Stage, when the analytical method employed is an optical measurement system, the user may employ utility subroutines that analyze the spectra series collected during the experiment. Individual IR, UV/Visible or other spectra may be accessed and analyzed independently. Alternatively, the user may select an entire series or a subset of a series to analyze in the identical manner. Such analyses typically involve selecting a baseline over a range of wavelengths, and then integrating the area within a spectral absorbance within another range of wavelengths. The spectral absorbances are normalized and recorded as a function of experiment time in a text data summary file. The text data file can be imported to suitable kinetics analysis software to derive rate expressions from the measured data. The Analysis Stage utility subroutines are accessed by the user in the software by clicking on a "Data Analysis" control button.

Examples of various other embodiments of this invention are described below. One embodiment of this invention is a method for testing a plurality of samples by (a) simultaneously reacting all samples with a fluid, and (b) during the simultaneous reaction of all samples, subjecting each sample in sequence to analysis. A further embodiment of this invention is a method for testing a plurality of samples by (a) simultaneously reacting all samples with a fluid, and (b) optically analyzing each sample using two or more optical methods, each method using light having a different wavelength in the range from about 190 nanometers to about 900 nanometers or in the range from about 2,500 nanometers to about 25,000 nanometers.

A further embodiment of this invention is a method for testing a plurality of samples by (a) changing the temperature of all samples in a first chamber, (b) simultaneously exposing all samples in a second chamber, which is isolated from the first chamber, to a reactive fluid, (c) analyzing each sample, and (d) after completion of analysis, changing the temperature of all samples in the first chamber. The temperature of the samples may be changed by simultaneously exposing the samples to a non-reactive fluid, and the temperature of the samples may in any step be increased or decreased, such as by at least about 100° C. An exemplary non-reactive fluid is nitrogen.

A further embodiment of this invention is an apparatus for testing a plurality of samples that contains (a) a reaction chamber in which all samples are reacted with a fluid, and (b) an analyzer that performs two or more optical methods, each method using light having a different wavelength in the range from about 190 nanometers to about 900 nanometers or in the range from about 2,500 nanometers to about 25,000 nanometers.

In the above embodiments, during the testing procedure, the samples may be reacted with a fluid in a chamber in which the temperature or the pressure is controlled. The fluid may be one or more gases and/or one or more liquids. Before reacting the samples with the fluid in a second chamber, the temperature of all samples may be changed in a first chamber, the first chamber being isolated from the second chamber. The temperature of all samples in the first chamber may also be changed after reacting the samples with the fluid. The temperature of the samples may, for example, be increased before the reaction, and decreased after the reaction, or vice versa. The first chamber may be isolated from the second chamber by sliding the sample carrier.

Another embodiment of this invention is an apparatus for testing a plurality of samples that contains (a) a fluid distribution system to simultaneously expose each sample to a reactive fluid, and (b) a transparent holder for one or more samples, and (c) an optical analyzer. Another embodiment of this invention is an apparatus for testing a plurality of samples that contains (a) a fluid distribution system to simultaneously expose each sample to a reactive fluid, and (b) a holder for one or more samples that comprises an attenuated total reflection crystal, and (c) an analyzer.

A further embodiment of this invention is an apparatus for testing a plurality of samples that contains (a) a first chamber in which all samples are simultaneously exposed to a non-reactive fluid, (b) a second chamber, isolated from the first chamber, in which all samples are simultaneously exposed to a reactive fluid, and (c) an analyzer. The non-reactive fluid or the reactive fluid may be a gas, and the non-reactive fluid may be nitrogen. A further embodiment of this invention is an apparatus for testing a plurality of samples that contains (a) a first chamber in which the temperature of all samples is changed by simultaneous exposure to fluid, (b) a second chamber, isolated from the first chamber, in which all samples are reacted by simultaneous exposure to a fluid, and (c) an analyzer.

A further embodiment of this invention is an apparatus for testing a plurality of samples, comprising (a) a first fluid distribution system to simultaneously expose all samples to a reactive fluid in a reaction chamber, (b) a second fluid distribution system to individually expose each sample in sequence to a reactive fluid in a reaction chamber, and (c) an analyzer. A reactive fluid may be a gas, and the reactive fluids may be different. The different fluid distribution systems are accessed by placing the sample holding positions under different ports in the outer body that are served by different fluid distribution manifolds.

In all of the embodiments described above, the analysis may be optical analysis, such as passing light waves through a sample, or reflecting light waves from a surface of a sample. Two or more optical methods may be used if desired, each method using light having a different wavelength in the range, for example, of from about 190 nanometers to about 900 nanometers or in the range from about 2,500 nanometers to about 25,000 nanometers. All optical methods may be performed simultaneously, and the analysis may be conducted during a simultaneous reaction of all samples. Other useful methods of analysis include sonic, ultrasonic, electrostatic, magnetic, radio frequency or x-ray analysis.

Those skilled in the art, having the benefit of the teachings of the present invention as set forth herein, may effect numerous modifications thereto.

What is claimed is:

1. A computer-controlled reaction apparatus for simultaneously conducting chemical reactions on a plurality of samples by maintaining the samples in chemical isolation from each other and subjecting each of the samples to substantially identical conditions, comprising:
   (a) a generally cylindrical reactor housing having a bore and a central axis, the housing comprised of:
      i) a loading/unloading section having an airlock;
      ii) a reaction section;
      iii) an analytical monitoring system;
      iv) a drive section;
      v) a distribution manifold system;
   (b) a gas-distribution and pressure control system in communication with the reactor housing;
   (c) a positioning system connected to the drive section;
   (d) a temperature control system for controlling the temperature of the reactor housing;
   (e) a reaction assembly, contained within the reactor housing, and movable in the housing bore in a direction along the axis of the housing, the reaction assembly comprising:
      i) a cylindrical outer body having a bore, a plurality of ports and a fluid distribution manifold;
      ii) a cylindrical inner body contained within the bore of the outer body and having:

A) a bore and a plurality of ports, and
B) a sample holder containing a plurality of sample holding positions for containing the samples to be reacted,
the sample holder being receivable within the bore of inner body and movable along the axis to a fully-inserted position, wherein, when the sample holder is in the fully-inserted position within the inner body, each of the plurality of reaction wells is aligned with each of the plurality of ports of the inner body;
(f) an analytical monitoring system comprising:
at least one optical port and at least one optical arrangement, comprising a paired source and detector, the at least one optical arrangement being capable of performing a measurement, at one or more ultraviolet, visible or infrared wavelengths, of a sample contained at a sample holding position to characterize the sample;
(g) a computer controller, connected to the gas-distribution and pressure control system, the positioning system, the temperature control system, and the analytical monitoring system;
wherein the reaction assembly is movable between the loading/unloading section, the reaction section, and the analytical monitoring system; and
wherein the drive section mechanically links the reaction assembly to the positioning system, so that the reaction assembly is positioned to each of a plurality of predetermined monitoring positions, such that at least one of the reaction wells is aligned with the at least one analytical port at each of the plurality of monitoring positions.

2. The apparatus of claim 1 wherein the computer controller comprises a central processor, connected by a data bus to a random access memory (RAM), a data storage device, an interface subsystem and a display device, the central processor being controlled by an operating system and application software stored in the data storage device, the central processor controlling the interface subsystem which is connected to, and controls, the gas-distribution and pressure control system, the positioning system, the temperature control system, and the optical monitoring system.

3. The apparatus of claim 1 wherein the gas-distribution and pressure control system comprises a supply of one or more gases, one or more valves and associated flow measuring devices and pressure regulators for controlling the flow of gas to the reaction assembly.

4. The apparatus of claim 1, wherein the temperature control system comprises one or more heating elements, one or more temperature sensors and a control unit, the control unit being electrically connected to the interface subsystem of the computer controller for receiving a temperature control signal and being connected to the one of more sensors for receiving temperature signals and being connected to the one of more heating elements for controlling electrical current to said heating elements.

5. The apparatus of claim 1 wherein the optical ports of the optical monitoring system are positioned in a coplanar arrangement so that an optical arrangement, comprising one or more ports, a optical source and an optical detector may be selected from a plurality of optical arrangements for characterizing each sample.

6. The apparatus of claim 1 wherein the optical monitoring system comprises a spectrophotometer.

7. The apparatus of claim 1 wherein the optical arrangement comprises a transmission arrangement, wherein light is transmitted through thin film samples.

8. The apparatus of claim 1 wherein the optical arrangement comprises a reflection arrangement, wherein light is reflected from at least one surface of thin film samples.

9. The apparatus of claim 1 wherein the optical arrangement comprises an attenuated total reflection arrangement, wherein light is repeatedly reflected from a surface of thin film samples.

10. A method of performing a plurality of chemical reactions using the apparatus of claim 1, comprising the steps of:
(a) positioning the reaction assembly at an initial undocked position in the loading/unloading section, loading the sample holder with samples to be reacted and inserting the sample holder into the inner body of the reaction assembly and closing the airlock,
(b) moving the inner body of the reactor assembly to a docked position within the outer body,
(c) causing the temperature control system to bring the reactor assembly to a predetermined temperature,
(d) causing the fluid distribution and pressure control system to introduce one or more reactant fluids at a predetermined flow rate and pressure to the samples within the sample holding positions,
(e) maintaining the fluid flow and pressure for a predetermined time so that a reaction occurs between the reactant fluids and the samples,
(f) sequentially positioning the reaction assembly so that each of the sample positions is aligned at each of the plurality of monitoring positions,
(g) performing at least one optical measurement to characterize each sample,
(h) returning the reaction assembly to the initial position in the loading/unloading section,
(i) quenching the reaction by stopping the flow of reactant fluids and initiating a flow of quenching gas to return the temperature and pressure of the reaction assembly to ambient,
(j) moving the inner body of the reactor assembly to the undocked position, and
(k) opening the airlock and removing the sample holder from the reactor assembly.

* * * * *